United States Patent
Hinze et al.

(10) Patent No.: US 7,332,519 B2
(45) Date of Patent: Feb. 19, 2008

(54) SPIROCYCLIC CYCLOHEXANE COMPOUNDS

(75) Inventors: Claudia Hinze, Aachen (DE); Bernd Sundermann, Aachen (DE); Stefan Oberboersch, Aachen (DE); Werner Englberger, Stolberg (DE); Elmark Friderichs, Stolberg (DE); Sven Frormann, Aachen (DE); Babette-Yvonne Koegel, Langerwehe (DE); Klaus Linz, Bonn (DE); Beatrix Merla, Aachen (DE); Derek Saunders, Aachen (DE); Wolfgang Schroeder, Aachen (DE); Hans Schick, Berlin (DE); Birgitta Henkel, Berlin (DE); Helmut Sonnenschein, Berlin (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 11/019,372

(22) Filed: Dec. 23, 2004

(65) Prior Publication Data

US 2005/0192333 A1    Sep. 1, 2005

(30) Foreign Application Priority Data

Dec. 23, 2003 (DE) .............................. 103 60 792

(51) Int. Cl.
*A61K 31/404* (2006.01)
*C07D 209/56* (2006.01)

(52) U.S. Cl. ................. 514/409; 548/407; 546/15; 546/18; 549/13; 549/43; 549/385; 514/278; 514/411; 514/437; 514/443; 514/454

(58) Field of Classification Search .............. 514/409, 514/278, 411, 437, 443, 454; 548/407; 546/15, 546/18; 549/13, 43, 385
See application file for complete search history.

(56) References Cited

FOREIGN PATENT DOCUMENTS

EP        0 466 548   *  1/1992

OTHER PUBLICATIONS

Rainer K. Reinscheid, et al., "Orphanin FQ: A Neuropeptide that Activates an Opoldlike G Protein-Coupled Receptor", Science, Nov. 3, 1995, pp. 792-794, vol. 270.
Miyuki Nishi, et al., "Unrestrained Nociceptive Response and Disregulation of Hearing Ability in Mice Lacking the Nociceptin/OrphaninFQ Receptor", The Embo Journal, 1997, pp. 1858-1864, vol. 16, No. 8, Oxford University Press.
J. S. Mogil, et al., "Orphanin FQ is a Functional Anti-Opoid Peptide", Letter to Neuroscience, Neuroscience, 1996, pp. 333-337, vol. 75, No. 2, Published by Elsevier Science Ltd., Great Britain, PII: S0306-4522(96)00338-7.
Jean-Claude Meunier, et al., "Isolation and Structure of the Endogenous Agonist of Opioid Receptor-Like $ORL_1$ Receptor", Nature, Letters to Nature, Oct. 12, 1995, pp. 532-535, vol. 377.
Michael A. King, et al., "Spinal Analgesic Activity of Orphanin FQ/Nociceptin and its Fragments", Neuroscience Letters, 1997, pp. 113-116, vol. 223, Elsevier Science Ireland Ltd.
Francois Jenck, et al., "Orphanin FQ Acts as an Anxiolytic to Attenuate Behavioral Responses to Stress", Proc. Natl. Acad. Sci., Dec. 1997, pp. 14854-14858, vol. 94.
Fuad A. Abdulla, et al., "Axotomy Reduces the Effect of Analgesic Opioids yet Increases the Effect of Nociceptin on Dorsal Root Ganglion Neurons", The Journal of Neuroscience, Dec. 1, 1998, pp. 9685-9694, vol. 18, No. 23, Society for Neuroscience.
Ali Ardati, et al., "Interaction of [$^3$H] Orphanin FQ and $^{125}$I-Tyr14-Orphanin FQ with the Orphanin FQ Receptor: Kinetics and Modulation by Cations and Guanine Nucleotides", Molecular Pharmacology, 1997, pp. 816-824, vol. 51, The American Society for Pharmacology and Experimental Therapeutics.
Toshiya Manabe, et al., "Facilitation of Long-Term Potentiation and Memory in Mice Lacking Nociceptin Receptors", Letters to Nature, Aug. 1998, pp. 577-581, vol. 394, Macmillan Publishers Ltd.
Calo' et al. "Pharmacology of Nociceptin and its receptor: a novel therapeutic target," *British Journal of Pharmacology*, 2000, pp. 1261-1283, vol. 129, No. 7, Macmillan Publishers Ltd.

* cited by examiner

Primary Examiner—Charanjit S. Aulakh
(74) Attorney, Agent, or Firm—Crowell & Moring LLP

(57) ABSTRACT

Spirocyclic cyclohexane compounds, methods for their production, pharmaceutical compositions containing these compounds, and the use of these spirocyclic cyclohexane compounds for treating conditions associated with the nociceptin/ORL1 receptor system, e.g. pain, drug withdrawal, anxiety, etc.

29 Claims, 1 Drawing Sheet

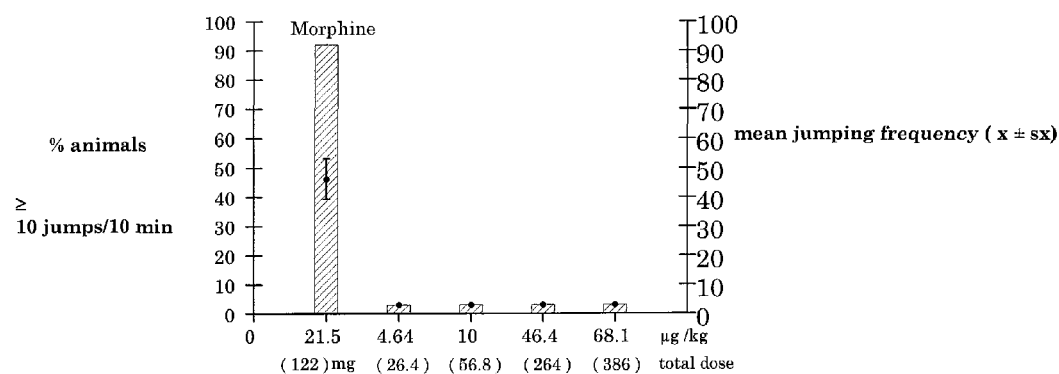

SPIROCYCLIC CYCLOHEXANE COMPOUNDS

CROSS REFERENCE TO RELATED APPLICATION

This application claims priority from Federal Republic of Germany patent application no. DE 103 60 792.7, filed Dec. 23, 2003, the entire disclosure of which is incorporated herein by reference.

BACKGROUND OF THE INVENTION

The present invention relates to spirocyclic cyclohexane compounds, to methods for their production, to pharmaceutical compositions containing these compounds and to the use of spirocyclic cyclohexane compounds for producing pharmaceutical compositions.

The heptadecapeptide nociceptin is an endogenous ligand of the ORL1 (Opioid-Receptor-Like)-receptor (Meunier et al., Nature 377, 1995, p. 532-535), which belongs to the family of opioid receptors and is found in many regions of the brain and the spinal cord and has high affinity for the ORL1 receptor. The ORL1 receptor is homologous to the μ, κ and δ opioid receptors, and the amino acid sequence of the nociceptin peptide has a pronounced similarity to those of the known opioid peptides. The activation of the receptor induced by the nociceptin leads, via the coupling with $G_{i/o}$ proteins to inhibition of adenylate cyclase (Meunier et al., Nature 377, 1995, p. 532-535).

After intercerebroventicular application, the nociceptin peptide exhibits pronociceptive and hyperalgesic activity in various animal models (Reinscheid et al., Science 270, 1995, p. 792-794). These findings can be explained as inhibition of stress-induced analgesia (Mogil et al., Neuroscience 75, 1996, p. 333-337). In this connection, anxiolytic activity of the nociceptin could also be demonstrated (Jenck et al., Proc. Natl. Acad. Sci. USA 94, 1997, 14854-14858).

On the other hand, an antinociceptive effect of nociceptin could also be demonstrated in various animal models, in particular after intrathecal application. Nociceptin has an antinociceptive effect in various pain models, for example in the tail flick test in mice (King et al., Neurosci. Lett., 223, 1997, 113-116). In models of neuropathic pain, an antinociceptive effect of nociceptin could also be detected, and was particularly beneficial since the effectiveness of nociceptin increases after axotomy of spinal nerves. This contrasts with conventional opioids, of which the effectiveness decreases under these conditions (Abdulla and Smith, J. Neurosci., 18, 1998, p. 9685-9694).

The ORL1 receptor is also involved in the regulation of further physiological and pathophysiological processes. These include inter alia learning and memory (Manabe et al., Nature, 394, 1997, p. 577-581), Hearing capacity (Nishi et al., EMBO J., 16, 1997, p. 1858-1864) and numerous further processes. A synopsis by Calo et al. (Br. J. Pharmacol. 129, 2000, 1261-1283) gives an overview of the indications or biological procedures, in which the ORL1-receptor plays a part or probably plays a part. Mentioned inter alia are: analgesics, stimulation and regulation of nutrient absorption, effect on μ-agonists such as morphine, treatment of withdrawal symptoms, reduction of the addiction potential of opioids, anxiolysis, modulation of motor activity, memory disorders, epilepsy; modulation of neurotransmitter release, in particular of glutamate, serotonin and dopamine, and therefore neurodegenerative diseases; influencing the cardiovascular system, triggering an erection, diuresis, antinatriuresis, electrolyte balance, arterial blood pressure, water retention disorders, intestinal motility (diarrhoea), relaxation of the respiratory tract, micturation reflex (urinary incontinence). The use of agonists and antagonists as anoretics, analgesics (also when administered with opioids) or nootropics is also discussed.

The possible applications of compounds that bind to the ORL1 receptor and activate or inhibit it are correspondingly diverse. In addition to this one, however, opioid receptors such as the μ receptor, but also the other subtypes of these opioid receptors, namely δ and κ, play a significant part in the field of pain therapy and also the other aforementioned indications. It is accordingly desirable if the compound also has an effect on these opioid receptors.

SUMMARY OF THE INVENTION

An object of the present invention was to provide substances which act on the nociceptin/ORL1 receptor system.

A further object of the invention was to provide substances which are suitable for pharmaceutical uses, particularly in pharmaceutical compositions for the treatment of the various diseases associated with the nociceptin/ORL1 receptor system and for use in the indications discussed above.

The invention therefore relates to spirocyclic cyclohexane compounds corresponding to the formula I,

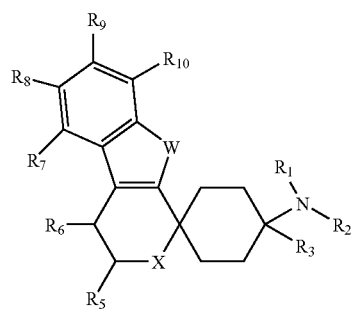

wherein $R^1$ and $R^2$ independently of one another represent H; CHO; respectively saturated or unsaturated, branched or unbranched, singly or multiply substituted or unsubstituted $C_{1-5}$ alkyl; respectively saturated or unsaturated, singly or multiply substituted or unsubstituted $C_{3-8}$ cycloalkyl; or respectively singly or multiply substituted or unsubstituted aryl, $C_{3-8}$ cycloalkyl or heteroaryl bound by $C_{1-3}$ alkyl; or the radicals $R^1$ and $R^2$ together represent $CH_2H_2OCH_2CH_2$, $CH_2CH_2NR^{11}CH_2CH_2$ or $(CH_2)_{3-6}$, wherein $R^{11}$ represents H; respectively saturated or unsaturated, branched or unbranched, singly or multiply substituted or unsubstituted $C_{1-5}$ alkyl; respectively saturated or unsaturated, singly or multiply substituted or unsubstituted $C_{3-8}$ cycloalkyl; respectively singly or multiply substituted or unsubstituted aryl or heteroaryl; or respectively singly or multiply substituted or unsubstituted aryl, $C_{3-8}$ cycloalkyl or heteroaryl bound by $C_{1-3}$ alkyl;

$R^3$ represents respectively unsubstituted or singly or multiply substituted heteroaryl or heteroaryl bound by $C_{1-3}$;

W represents $NR^4$, O or S, and $R^4$ represents H; saturated or unsaturated, branched or unbranched, unsubstituted or singly or multiply substituted $C_{1-5}$ alkyl; respectively substituted or unsubstituted aryl or heteroaryl; respectively singly or multiply substituted or unsubstituted aryl, heteroaryl or cycloalkyl bound by a $C_{1-3}$ alkyl group; $COR^{12}$; $SO_2R^{12}$,
  wherein $R^{12}$ represents H; respectively saturated or unsaturated, branched or unbranched, singly or multiply substituted or unsubstituted $C_{1-5}$ alkyl; respectively saturated or unsaturated, singly or multiply substituted or unsubstituted $C_{3-8}$ cycloalkyl; respectively singly or multiply substituted or unsubstituted aryl or heteroaryl; or respectively singly or multiply substituted or unsubstituted aryl, $C_{3-8}$ cycloalkyl or heteroaryl bound by $C_{1-3}$ alkyl; $OR^{13}$; $NR^{14}R^{15}$;

$R^5$ represents =O; H; saturated or unsaturated, branched or unbranched, unsubstituted or singly or multiply substituted $C_{1-5}$ alkyl; $COOR^{13}$, $CONR^{13}$, $OR^{13}$; saturated or unsaturated, unsubstituted or singly or multiply substituted $C_{3-8}$ cycloalkyl; unsubstituted or singly or multiply substituted aryl or heteroaryl; or unsubstituted or singly or multiply substituted aryl, $C_{3-8}$ cycloalkyl or heteroaryl bound by $C_{1-3}$ alkyl;

$R^6$ represents H; F, Cl, $NO_2$, $CF_3$, $OR^{13}$, $SR^{13}$, $SO_2R^{13}$, $SO_2OR^{13}$, CN, $COOR^{13}$, $NR^{14}R^{15}$; saturated or unsaturated, branched or unbranched, unsubstituted or singly or multiply substituted $C_{1-5}$ alkyl; saturated or unsaturated, unsubstituted or singly or multiply substituted $C_{3-8}$ cycloalkyl; unsubstituted or singly or multiply substituted aryl or heteroaryl; or unsubstituted or singly or multiply substituted aryl, $C_{3-8}$ cycloalkyl or heteroaryl bound by $C_{1-3}$ alkyl; or $R^5$ and $R^6$ together represent $(CH_2)_n$ where n=2, 3, 4, 5 or 6, wherein individual hydrogen atoms may also be replaced by F, Cl, Br, I, $NO_2$, $CF_3$, $OR^{13}$, CN or $C_{1-5}$ alkyl;

$R^7$, $R^8$, $R^9$ and $R^{10}$, independently of one another, represent H, F, Cl, Br, I, $NO_2$, $CF_3$, $OR^{13}$, $SR^{13}$, $SO_2R^{13}$, $SO_2OR^{13}$, CN, $COOR^{13}$ $NR^{14}R^{15}$; unsubstituted or singly or multiply substituted $C_{1-5}$ alkyl, $C_{3-8}$ cycloalkyl; unsubstituted or singly or multiply substituted aryl or heteroaryl; or unsubstituted or singly or multiply substituted aryl, $C_{3-8}$ cycloalkyl or heteroaryl bound by $C_{1-3}$ alkyl;
  wherein $R^{13}$ represents H; respectively saturated or unsaturated, branched or unbranched, unsubstituted or singly or multiply substituted $C_{1-5}$ alkyl; respectively saturated or unsaturated, unsubstituted or singly or multiply substituted $C_{3-8}$ cycloalkyl; unsubstituted or singly or multiply substituted aryl or heteroaryl; or unsubstituted or singly or multiply substituted aryl, $C_{3-8}$ cycloalkyl or heteroaryl bound by $C_{1-3}$ alkyl,
  $R^{14}$ and $R^{15}$ independently of one another represent H; respectively saturated or unsaturated, branched or unbranched, unsubstituted or singly or multiply substituted $C_{1-5}$ alkyl; respectively saturated or unsaturated, unsubstituted or singly or multiply substituted $C_{3-8}$ cycloalkyl; unsubstituted or singly or multiply substituted aryl or heteroaryl; or unsubstituted or singly or multiply substituted aryl, $C_{3-8}$ cycloalkyl or heteroaryl bound by $C_{1-3}$ alkyl, or
  $R^{14}$ and $R^{15}$ together form $CH_2CH_2OCH_2CH_2$, $CH_2CH_2NR^{16}CH_2CH_2$ or $(CH_2)_{3-6}$,
    wherein $R^{16}$ represents H; saturated or unsaturated, branched or unbranched, unsubstituted or singly or multiply substituted $C_{1-5}$ alkyl; and X represents O, S, SO, $SO_2$ or $NR^{17}$;
  wherein $R^{17}$ represents H; $C_{1-5}$ alkyl, saturated or unsaturated, branched or unbranched; $COR^{12}$ or $SO_2R^{12}$, in the form of the racemate; the enantiomers, diastereomers, mixtures of the enantiomers or diastereomers or an individual enantiomer or diastereomer; the bases and/or salts of physiologically acceptable acids or cations.

When combining various radicals, for example $R^7$, $R^8$, $R^9$ and $R^{10}$, and when combining radicals on their substituents, such as $OR^{13}$, $SR^{13}$, $SO_2R^{13}$ or $COOR^{13}$, a substituent, for example $R^{13}$, can assume different meanings for two or more radicals, for example $R^7$, $R^8$, $R^9$ and $R^{10}$, within a substance.

The compounds according to the invention exhibit good binding to the ORL1 receptor and also to other opioid receptors.

As used herein, the terms "$C_{1-5}$ alkyl" and "$C_{1-3}$ alkyl" include acyclic saturated or unsaturated hydrocarbon radicals, which may be branched or straight-chained and unsubstituted or singly or multiply substituted, with 1, 2, 3, 4 or 5 carbon atoms or 1, 2 or 3 carbon atoms, i.e. $C_{1-5}$ alkanyls, $C_{2-5}$ alkenyls and $C_{2-5}$ alkinyls or $C_{1-3}$ alkanyls, $C_{2-3}$ alkenyls and $C_{2-3}$ alkinyls. Alkenyls have at least one C—C double bond and alkinyls at least one C—C triple bond. Alkyl is advantageously selected from the group comprising methyl, ethyl, n-propyl, 2-propyl, n-butyl, iso-butyl, sec.-butyl, tertiary-butyl, n-pentyl, iso-pentyl, neo-pentyl, n-hexyl, 2-hexyl; ethylenyl(vinyl), ethinyl, propenyl(—$CH_2CH=CH_2$, —CH=CH—$CH_3$, —C(=$CH_2$)—$CH_3$), propinyl(—CH—C≡CH, —C≡C—$CH_3$), 1,1-dimethylethyl, 1,1-dimethylpropyl, butenyl, butinyl, pentenyl and pentinyl.

For the purposes of this invention the term "cycloalkyl" or "$C_{3-8}$ cycloalkyl" denotes cyclic hydrocarbons with 3, 4, 5, 6, 7 or 8 carbon atoms, wherein the hydrocarbons may be saturated or unsaturated (but not aromatic), unsubstituted or singly or multiply substituted. With respect to cycloalkyl, the term also comprises saturated or unsaturated (but not aromatic) cycloalkyls, in which one or two carbon atoms are replaced by a heteroatom, S, N or O. $C_{3-8}$ cycloalkyl is advantageously selected from the group comprising cyclopropyl, cyclobutyl, cyclopentyl, cyclohexyl, cycloheptyl, cyclooctyl, cyclopentenyl, cyclohexenyl, cycloheptenyl and cyclooctenyl, and also tetrahydropyranyl, dioxanyl, dioxolanyl, morpholinyl, piperidinyl, piperazinyl, pyrazolinonyl and pyrrolidinyl.

The term $(CH_2)_{3-6}$ refers to —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and $CH_2$—$CH_2$—$CH_2$—$CH_2$—$CH_2$—$CH_2$—.

The term "aryl", according to this invention, denotes carbocyclic ring systems comprising at least one aromatic ring, but without a heteroatom in only one of the rings, inter alia phenyls, naphthyls and phenanthrenyls, fluoranthenyls, fluorenyls, indanyls and tetralinyls. The aryl radicals can also be condensed with further saturated, (partially) unsaturated or aromatic ring systems. Each aryl radical can be unsubstituted or singly or multiply substituted, wherein the aryl substituents may be the same or different and in any desired or possible position of the aryl. Phenyl- or naphthyl radicals are particularly advantageous.

The term "heteroaryl" represents a 5-, 6- or 7-membered cyclic aromatic radical, which contains at least 1, optionally also 2, 3, 4 or 5 heteroatoms, wherein the heteroatoms may be the same or different and the heterocycle unsubstituted or singly or multiply substituted. If the heterocycle is substituted, the substituents may be the same or different and in any desired, possible position of the heteroaryl. The heterocycle may also be part of a bicyclic or polycyclic system. Preferred heteroatoms include nitrogen, oxygen and sulfur. It is preferred that the heteroaryl radical is selected from the group consisting of pyrrolyl, indolyl, furyl(furanyl), benzofuranyl, thienyl(thiophenyl), benzothienyl, benzothiadiazolyl, benzothiazolyl, benzotriazolyl, benzodioxolanyl, benzodioxanyl, phtalazinyl, pyrazolyl, imidazolyl, thiazolyl, oxazolyl, isoxazoyl, pyridinyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl or oxadiazolyl, wherein the bond to the compounds of general structure I may be effected by any desired, possible ring member of the heteroaryl radical.

In connection with "alkyl", the term "substituted" according to this invention is taken to mean the replacement of one or more hydrogen radicals by F, Cl, Br, I, —CN, $NH_2$, NH-alkyl, NH-aryl, NH-heteroaryl, NH-cycloalkyl, NH-alkyl aryl, NH-alkyl heteroaryl, NH-alkyl-OH, $N(alkyl)_2$, $N(alkyl\ aryl)_2$, $N(alkyl\ heteroaryl)_2$, $N(cycloalkyl)_2$, $N(alkyl-OH)_2$, $NO_2$, SH, S-alkyl, S-aryl, S-heteroaryl, S-alkyl aryl, S-alkyl heteroaryl, S-cycloalkyl, S-alkyl-OH, S-alkyl SH, OH, O-alkyl, O-aryl, O-heteroaryl, O-alkyl aryl, O-alkyl heteroaryl, O-cycloalkyl, O-alkyl-OH, CHO, $C(=O)C_{1-6}$ alkyl, $C(=S)C_{1-6}$-alkyl, $C(=O)$aryl, $C(=S)$ aryl, $C(=O)C_{1-6}$ alkyl aryl, $C(=S)C_{1-6}$ alkyl aryl, $C(=O)$-heteroaryl, $C(=S)$-heteroaryl, $C(=O)$-cycloalkyl, $C(=S)$-cycloalkyl, $CO_2H$, $CO_2$-alkyl, $CO_2$-alkyl aryl, $C(=O)NH_2$, $C(=O)NH$-alkyl, $C(=O)NH$-aryl, $C(=O)NH$-cycloalkyl, $C(=O)N(alkyl)_2$, $C(=O)N(alkyl\ aryl)_2$, $C(=O)N(alkyl\ heteroaryl)_2$, $C(=O)N(cycloalkyl)_2$, SO-alkyl, $SO_2$-alkyl, $SO_2NH_2$, $SO_3H$, $PO(O-C_{1-6}$-alkyl$)_2$, $Si(C_{1-6}$ alkyl$)_3$, $Si(C_{3-8}$ cycloalkyl$)_3$, $Si(CH_2-C_{3-8}$ cycloalkyl$)_3$, $Si(phenyl)_3$, cycloalkyl, aryl or heteroaryl, wherein multiply substituted radicals are taken to mean radicals which are either multiply, for example doubly or trebly, substituted on different atoms or the same atoms, for example trebly on the same C atom, as in the case of $CF_3$ or —$CH_2CF_3$ or at different positions, as in the case of —CH(OH)—CH=CHCHCl$_2$. Multiple substitution can take place with the same substituent or with different substituents. A substituent may optionally also in turn be substituted; thus —O-alkyl also includes inter alia —O—$CH_2$—$CH_2$—O—$CH_2$—$CH_2$—OH.

With respect to "aryl", "heteroaryl" and "cycloalkyl", according to this invention, "singly or multiply substituted" is taken to mean single or multiple, for example double, treble, quadruple or quintuple, substitution of one or more hydrogen atoms of the ring system by F, Cl, Br, I, CN, $NH_2$, NH-alkyl, NH-aryl, NH-heteroaryl, NH-alkyl aryl, NH-alkyl heteroaryl, NH-cycloalkyl, NH-alkyl-OH, $N(alkyl)_2$, $N(alkyl\ aryl)_2$, $N(alkyl\ heteroaryl)_2$, $N(cycloalkyl)_2$, $N(alkyl-OH)_2$, $NO_2$, SH, S-alkyl, S-cycloalkyl, S-aryl, S-heteroaryl, S-alkyl aryl, S-alkyl heteroaryl, S-cycloalkyl, S-alkyl-OH, S-alkyl SH, OH, O-alkyl, O-cycloalkyl, O-aryl, O-heteroaryl, O-alkyl aryl, O-alkyl heteroaryl, O-cycloalkyl, O-alkyl-OH, CHO, $C(=O)C_{1-6}$ alkyl, $C(=S)C_{1-6}$ alkyl, $C(=O)$aryl, $C(=S)$aryl, $C(=O)-C_{1-6}$ alkyl aryl, $C(=S)C_{1-6}$ alkyl aryl, $C(=O)$-heteroaryl, $C(=S)$-heteroaryl, $C(=O)$-cycloalkyl, $C(=S)$-cycloalkyl, $CO_2H$, $CO_2$-alkyl, $CO_2$-alkyl-aryl, $C(=O)NH_2$, $C(=O)NH$-alkyl, $C(=O)NH$-aryl, $C(=O)NH$-cycloalkyl, $C(=O)N(alkyl)_2$, $C(=O)N(alkyl\ aryl)_2$, $C(=O)N(alkyl\ heteroaryl)_2$, $C(=O)N(cycloalkyl)_2$, S(O)-alkyl, S(O)-aryl, $SO_2$-alkyl, $SO_2$-aryl, $SO_2NH_2$, $SO_3H$, $CF_3$, =O, =S; alkyl, cycloalkyl, aryl and/or heteroaryl; on one atom or optionally on different atoms (wherein a substituent can, in turn, optionally be substituted). Multiple substitution takes place here using the same or different substituents.

The term "salt" refers to any form of the active ingredient according to the invention in which it assumes a charged or ionic form and is coupled to a counter ion (a cation or an anion) or is in solution. This also includes complexes of the active ingredient with other molecules and ions, in particular complexes complexed by ionic interactions. In particular this is taken to mean (and this is also a preferred embodiment of this invention) physiologically acceptable salts, in particular physiologically acceptable salts with cations or bases and physiologically acceptable salts comprising anions or acids or even a salt formed with a physiologically acceptable acid or a physiologically acceptable cation.

As used herein, the term "physiologically acceptable salt with anions or acids" means salts of at least one of the compounds of the invention—usually protonated, for example on nitrogen—as a cation with at least one anion, which are physiologically acceptable—in particular when administered to humans and/or mammals. In particular, according to this invention, this is taken to mean the salt formed with a physiologically acceptable acid, namely salts of the respective active ingredient with inorganic or organic acids, which are physiologically acceptable—in particular when administered to humans and/or mammals. Examples of physiologically acceptable salts of specific acids are salts of: hydrochloric acid, hydrobromic acid, sulfuric acid, methane sulfonic acid, formic acid, acetic acid, oxalic acid, succinic acid, maleic acid, tartaric acid, mandelic acid, fumaric acid, lactic acid, citric acid, glutamic acid, saccharic acid, monomethyl sebacic acid, 5-oxo-proline, hexane-1-sulfonic acid, nicotinic acid, 2-, 3- or 4-amino benzoic acid, 2,4,6-trimethyl-benzoic acid, α-lipoic acid, acetyl glycine, acetyl salicylic acid, hippuric acid and/or aspartic acid. The hydrochloride salt, the citrate and the hemicitrate are particularly preferred.

The term "salt formed with a physiologically acceptable acid", according to this invention, means salts of the respective active ingredient with inorganic or organic acids, which are physiologically acceptable—in particular when applied to humans and/or mammals. Hydrochloride and citrate are particularly preferred. Examples of physiologically acceptable acids include: hydrochloric acid, hydrobromic acid, sulfuric acid, methane sulfonic acid, formic acid, acetic acid, oxalic acid, succinic acid, tartaric acid, mandelic acid, fumaric acid, lactic acid, citric acid, glutamic acid, saccharic acid, monomethyl sebacic acid, 5-oxo-proline, hexane-1-sulfonic acid, nicotinic acid, 2-, 3- or 4-amino benzoic acid, 2,4,6-trimethyl benzoic acid, α-lipoic acid, acetylglycine, hippuric acid and/or aspartic acid.

The term "physiologically acceptable salt with cations or bases," according to this invention, means a salt of at least one of the compounds according to the invention—usually a (deprotonated) acid—as an anion with at least one, preferably inorganic, cation, which are physiologically acceptable, in particular when applied to humans and/or mammals. The salts of the alkali and alkaline earth metals are preferred, and also ammonium salts, in particular however (mono) or (di)sodium, (mono) or (di)potassium, magnesium or calcium salts.

The term "salt formed with a physiologically acceptable cation" is taken to mean, according to this invention, salts of at least one of the respective compounds as an anion with at least one inorganic cation, which are physiologically acceptable, in particular when applied to humans and/or mammals. The salts of the alkali and alkaline earth metals are particularly preferred, as are ammonium salts, in particular (mono) or (di)sodium, (mono) or (di)potassium, magnesium or calcium salts.

In a preferred embodiment of the spirocyclic cyclohexane compounds according to the invention, $R^1$ and $R^2$, independently of one another, represent H; respectively saturated or unsaturated, branched or unbranched, singly or multiply substituted or unsubstituted $C_{1-2}$ alkyl; or the radicals $R^1$ and $R^2$ together represent $CH_2H_2OCH_2CH_2$, $CH_2CH_2NR^{11}CH_2CH_2$ or $(CH_2)_{3-6}$.

In a further preferred embodiment of the spirocyclic cyclohexane compounds according to the invention, $R^1$ and $R^2$, independently of one another, represent H; branched or unbranched, saturated or unsaturated, unsubstituted or singly or multiply substituted $C_{1-5}$ alkyl, or CHO; $R^3$ represents unsubstituted or singly or multiply substituted heteroaryl; $R^5$ represents H, branched or unbranched, unsubstituted or singly or multiply substituted $C_{1-5}$ alkyl, or $COOR^{13}$; $R^6$ represents H or $C_{1-5}$ alkyl; and $R^7$, $R^8$, $R^9$ and $R^{10}$, independently of one another, represent H; branched or unbranched, unsubstituted or singly or multiply substituted $C_{1-5}$ alkyl; F, Cl, Br, I, OH, $OCH_3$, $NH_2$, COOH, $COOCH_3$, $NHCH_3$ or $N(CH_3)_2$ or $NO_2$.

Also preferred according to the invention are spirocyclic cyclohexane compounds of formula I, wherein W represents $NR^4$, O or S, and X represents O, S, SO, $SO_2$ or $NR^{17}$, preferably O or $NR^{17}$; $R^1$ and $R^2$ independently of one another represent H; branched or unbranched, singly or multiply substituted or unsubstituted $C_{1-4}$ alkyl, or CHO; $R^3$ represents unsubstituted or singly or multiply substituted heteroaryl; $R^4$ represents H; singly or multiply substituted or unsubstituted $C_{1-3}$ alkyl, or $CO(CH_2)_mH$, wherein m=0 to 2, and/or $R^5$ and $R^6$ each represent H, and/or $R^7$, $R^8$, $R^9$ and $R^{10}$, independently of one another, represent H; respectively branched or unbranched, saturated or unsaturated, unsubstituted or singly or multiply substituted $C_{1-5}$ alkyl or $OC_{1-3}$ alkyl; F, Cl, Br, I, $CF_3$, OH, SH, $SCH_3$, $OCH_3$, $NH_2$, COOH, $COOCH_3$, $NHCH_3$ or $N(CH_3)_2$ or $NO_2$. Compounds in which W represents $NR^4$ and X represents O are particularly preferred.

In a particularly preferred embodiment of the spirocyclic cyclohexane compounds according to the invention $R^1$ and $R^2$ independently of one another represent H or $CH_3$, wherein $R^1$ and $R^2$ are not simultaneously H.

In another particularly preferred embodiment of the spirocyclic cyclohexane compounds according to the invention $R^3$ represents thienyl or pyridyl.

In a more particularly preferred embodiment of the spirocyclic cyclohexane compounds according to the invention the radical $R^5$ represents H, $CH_3$, $COOCH_3$ or $CH_2OH$; the radical $R^6$ represents H; and $R^7$, $R^8$, $R^9$ and $R^{10}$, independently of one another, represent H; branched or unbranched, unsubstituted or singly or multiply substituted $C_{1-5}$ alkyl; F, Cl, Br, I, $CF_3$, OH, $OCH_3$, $NH_2$, COOH, $COOCH_3$, $NHCH_3$ or $N(CH_3)_2$ or $NO_2$. Preferably, the radicals $R^6$, $R^7$, $R^8$, $R^9$ and $R^{10}$ represent H; or one of the radicals $R^6$, $R^7$, $R^8$ represents branched or unbranched, unsubstituted or singly or multiply substituted $C_{1-5}$ alkyl; F, Cl, Br, I, OH, $OCH_3$, COOH, $COOCH_3$, $NH_2$, $NHCH_3$ or $N(CH_3)_2$ or $NO_2$, while the other radicals are H; or two of the radicals $R^6$, $R^7$, $R^8$, $R^9$ and $R^{10}$, independently of one another, represent H; branched or unbranched, unsubstituted or singly or multiply substituted $C_{1-5}$ alkyl; F, Cl, Br, I, OH, $OCH_3$, COOH, $COOCH_3$, $NH_2$, $NHCH_3$ or $N(CH_3)_2$ or $NO_2$, while the other radicals are H.

Also particularly preferred are compounds in which W represents $NR^4$, X represents O, and $R^4$ represents H, $CH_3$, $C_2H_5$, acetyl, phenyl, benzyl or $COR^{12}$, preferably H.

In a particularly preferred embodiment of the spirocyclic cyclohexane compounds according to the invention $R^1$ and $R^2$ independently of one another represent H or $CH_3$, in particular $CH_3$; $R^3$ represents pyridyl or thienyl, and/or the radicals $R^5$, $R^6$, $R^7$, $R^9$ and $R^{10}$ represent H, and the radical $R^8$ represents H or F.

More particularly preferred are spirocyclic cyclohexane compounds selected from the group consisting of:

1,1-[3-dimethylamino-3-(pyridin-2-yl)pentamethylene]-3,4-dihydro-1H-2,9-diazafluorene, 2-acetyl-1,1-[3-dimethylamino-3-(pyridin-2-yl)pentamethylene]-3,4-dihydro-1H-2,9-diazafluorene, 1,1-[3-dimethylamino-3-(pyridin-2-yl)pentamethylene]-3,4-dihydro-1H-2-oxa-9-thiafluorene, 1,1-[3-dimethylamino-3-(pyridin-2-yl)pentamethylene]-1,3,4,9-tetrahydropyrano-[3,4-b]indole hemicitrate, non-polar diastereoisomer, 1,1-[3-dimethylamino-3-(pyridin-2-yl)pentamethylene]-1,3,4,9-tetrahydropyrano-[3,4-b]indole citrate, polar diastereoisomer, 1,1-[3-dimethylamino-3-(2-thienyl)pentamethylene]-1,3,4,9-tetrahydro-pyrano[3,4-b]indole dimethanesulfonate, 1,1-[3-dimethylamino-3-(2-thienyl)pentamethylene]-1,3,4,9-tetrahydro-pyrano[3,4-b]indole citrate, 1,1-[3-dimethylamino-3-(3-thienyl)pentamethylene]-1,3,4,9-tetrahydro-pyrano[3,4-b]indole hemicitrate, 1,1-[3-dimethylamino-3-(3-thienyl)pentamethylene]-1,3,4,9-tetrahydro-pyrano[3,4-b]indole citrate, 1,1-[3-dimethylamino-3-(2-thienyl)pentamethylene]-1,3,4,9-tetrahydro-pyrano[3,4-b]-6-fluoroindole hemicitrate, 1,1-[3-dimethylamino-3-(2-thienyl)pentamethylene]-1,3,4,9-tetrahydro-pyrano[3,4-b]-6-fluoroindole citrate, 1,1-[3-dimethylamino-3-(3-thienyl)pentamethylene]-1,3,4,9-tetrahydro-pyrano[3,4-b]-6-fluoroindole dimethanesulfonate, 1,1-[3-dimethylamino-3-(3-thienyl)pentamethylene]-1,3,4,9-tetrahydro-pyrano[3,4-b]-6-fluoroindole hemicitrate, 1,1-[3-methylamino-3-(2-thienyl)pentamethylene]-1,3,4,9-tetrahydro-pyrano[3,4-b]indole citrate, 1,1-[3-methylamino-3-(2-thienyl)pentamethylene]-1,3,4,9-tetrahydro-pyrano[3,4-b]-6-fluoroindole citrate, 1,1-[3-methylamino-3-(3-thienyl)pentamethylene]-1,3,4,9-tetrahydro-pyrano[3,4-b]indole citrate, and 1,1-[3-methylamino-3-(3-thienyl)pentamethylene]-1,3,4,9-tetrahydro-pyrano[3,4-b]-6-fluoroindole citrate, or a mixture of two or more of the foregoing.

The substances according to the invention act, for example, on the ORL1 receptor that is relevant in connection with various diseases, so they are suitable as a pharmaceutical active ingredient in a pharmaceutical composition. The invention therefore also relates to pharmaceutical compositions containing at least one spirocyclic cyclohexane compound according to the invention and at least one other ingredient, optionally suitable additives and/or auxiliary agents and/or optionally further active ingredients.

The pharmaceutical compositions according to the invention optionally contain, in addition to at least one spirocyclic cyclohexane compound according to the invention, suitable additives and/or auxiliary agents, therefore also excipients, fillers, solvents, diluents, dyes and/or binders and can be administered as liquid pharmaceutical preparations in the form of injection solutions, drops or syrups, as semi-solid pharmaceutical preparations in the form of granules, tablets, pellets, patches, capsules, plasters/spray plasters or aerosols. The choice of auxiliary agents, etc., and the quantities thereof to be used depend on whether the pharmaceutical preparation is to be applied orally, perorally, parenterally, intravenously, intraperitoneally, intradermally, intramuscularly, intranasally, buccally, rectally or topically, for example to the skin, the mucous membranes or the eyes. Preparations in the form of tablets, dragees, capsules, granules, drops, juices and syrups are suitable for parenteral administration, topical and inhalative application solutions, suspensions, easily reconstituted dry preparations and sprays for parenteral administration. Spirocyclic cyclohexane compounds according to the invention in a depot, in dissolved form or in a plaster, optionally with the addition of agents to promote skin penetration, are suitable percutaneous application preparations. Forms of preparation which can be administered orally or percutaneously can release the spirocyclic cyclohexane compounds according to the invention slowly. The spirocyclic cyclohexane compounds according to the invention can also be administered in the form of parenteral long-acting repositories such as implants or implanted pumps. In principle, further active ingredients known to the person skilled in the art can be added to the pharmaceutical preparations according to the invention.

The amount of active ingredient to be administered to the patient varies as a function of the weight of the patient, the method of administration, the indication for which given, and the severity of the illness. Typically, 0.00005 to 50 mg/kg, preferably 0.001 to 0.5 mg/kg, of at least one spirocyclic cyclohexane compound according to the invention is administered.

With all of the above forms of the pharmaceutical compositions according to the invention it is particularly preferred if the pharmaceutical composition contains, in addition to at least one spirocyclic cyclohexane compound, a further active ingredient, in particular an opioid, preferably a strong opioid, in particular morphine, or an anaesthetic, preferably hexobarbital or halothane.

In a preferred form of the pharmaceutical composition, a spirocyclic cyclohexane compound contained according to the invention is present as a pure diastereomer and/or enantiomer, as a racemate or as a non-equimolar or equimolar blend of the diastereomers and/or enantiomers.

As noted above, the ORL1 receptor has been identified in particular as involved in the occurrence of pain. Spirocyclic cyclohexane compounds according to the invention can accordingly be used for producing a pharmaceutical composition for the treatment of pain, in particular acute, neuropathic or chronic pain. The invention therefore also relates to the use of a spirocyclic cyclohexane compound according to the invention for treating pain, in particular acute, visceral, neuropathic or chronic pain.

Pharmacological experiments have shown that the spirocyclic cyclohexane compounds are useful for the treatment of opioid abuse, but also as muscle relaxant or anesthetic. The invention therefore also relates to the use of a spirocyclic cyclohexane compound according to the invention for the treatment of withdrawal symptoms, alcohol and/or drug and/or medicine abuse and/or dependency, as a muscle relaxant or anaesthetic or for co-administration in treatment with an opioid analgesic or anaesthetic, for the treatment of withdrawal symptoms and/or for reducing the addiction potential of opioids.

The invention also relates to the use of a spirocyclic cyclohexane compound according to the invention for the treatment of anxiety, stress and stress-related syndromes, depression, epilepsy, Alzheimer's disease, senile dementia, general cognitive dysfunction, learning and memory disorders (as a nootropic), sexual dysfunction, cardiovascular diseases, hypotension, hypertension, tinnitus, pruritus, migraine, hearing difficulties, deficient intestinal motility, impaired nutrients absorption, anorexia, obesity, locomotive disorders, diarrhoea, cachexia, urinary incontinence or as a anti-convulsive, for diuresis or anti-natriuresis, anxiolysis, for modulation of motor activity or for modulation of neurotransmitter release and treatment of neurodegenerative diseases associated therewith. Advantageously, the spirocyclic cyclohexane compound may be present in the form of a pure diastereomer and/or enantiomer, as a racemate or as a non-equimolar or equimolar blend of the diastereomers and/or enantiomers.

The invention also relates to a method for the treatment, in particular in one of said indications, of a non-human mammal or humans, which or who requires treatment of pain, in particular chronic pain, by administration of a therapeutically effective dose of a spirocyclic derivative according to the invention, or of a pharmaceutical preparation according to the invention.

The invention also relates to a process for producing the spirocyclic cyclohexane compounds according to the invention as stated in detail in the following description and examples. A particularly suitable process, hereinafter called the main process, for producing a spirocyclic cyclohexane compound according to the invention is described below.

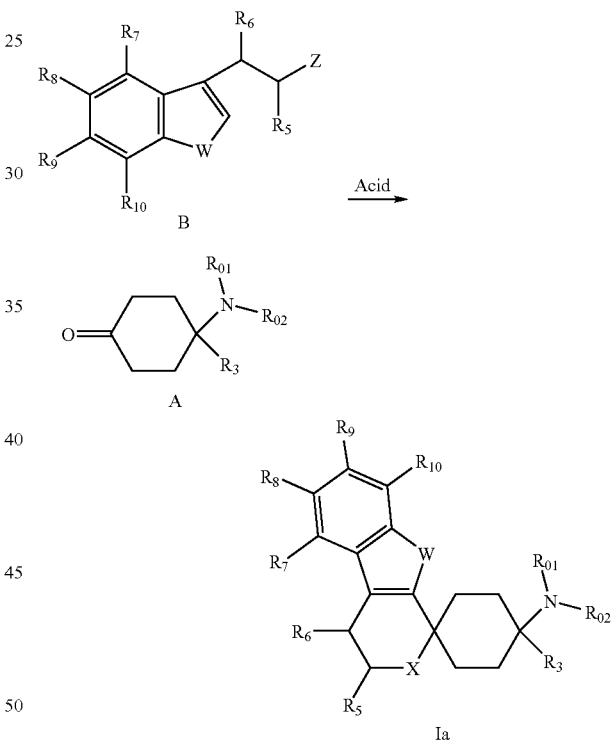

$Z = XY$
$Y = H, SiMe_3$

To produce the a compound corresponding to formula Ia, in which X, W, $R^1$, $R^2$, $R^3$, $R^5$, $R^6$, $R^7$, $R^8$, $R^9$ and $R^{10}$ have the meanings given above for the compounds corresponding to formula I, and $R^{01}$ and $R^{02}$ have the meanings given for $R^1$ and $R^2$ in the compounds according to formula I and in addition, independently of one another, can represent a protective group, a ketone corresponding to formula A is reacted with a heteroaromatic compound corresponding to formula B with addition of an acid or a trimethylsilylester thereof, for example trifluoromethanesulfonic acid trimethylsilylester, acetic acid, phosphoric acid, methane sulfonic acid or trifluoroacetic acid in a suitable solvent, for example dichloroethane, dichloromethane, chloroform, acetonitrile, diethyl ether or nitromethane.

The production of suitable 4-aminocyclohexanones is known from the literature (e.g., from Lednicer et al., J. Med. Chem., 23, 1980, 424-430; WO 0290317; and/or U.S. Pat. No. 4,065,573).

Alternatively, compounds according to the invention may be produced according to the following pattern:

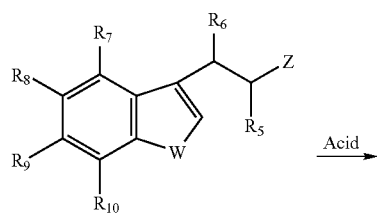

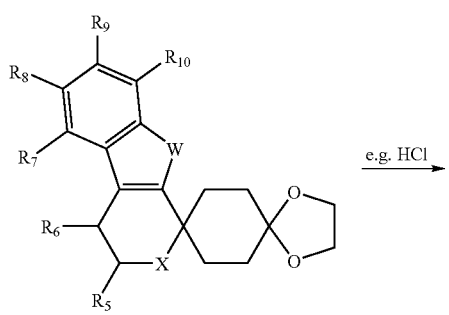

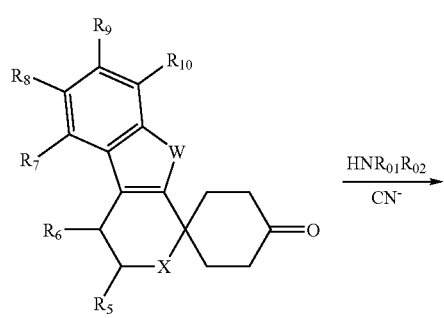

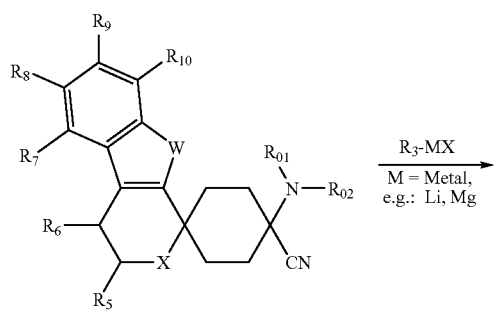

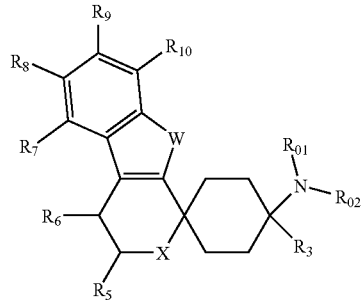

Z = XY
Y = H, SiMe₃ wherein X, W, $R^3$, $R^5$, $R^6$, $R^7$, $R^8$, $R^9$ and $R^{10}$ have the meanings given above for compounds corresponding to formula I, and $R^{01}$ and $R^{02}$ have the meanings given above for $R^1$ and $R^2$ in compounds according to formula I and in addition, independently of one another, can represent a protective group.

Spirocyclic cyclohexane compounds corresponding to formula I, wherein X represents $NR^{17}$ and $R^{17}$ represents $COR^{12}$ or $SO_2R^{12}$, can be obtained by reacting a spirocyclic cyclohexane compound of formula I, wherein X represents NH, with an anhydride or an acid chloride with addition of a base, for example triethylamine. The reaction is preferably carried out with microwave irradiation.

Spirocyclic cyclohexane compounds corresponding to formula I, wherein X represents SO or $SO_2$, can be obtained by reacting a spirocyclic cyclohexane compound corresponding to formula I, wherein X represents S, with an oxidizing agent, for example $H_2O_2$.

Spirocyclic cyclohexane compounds in which $R^3$ represents 3-thienyl, $R^1$ represents $CH_3$ and $R^2$ represents H, may be produced in accordance with the following description, R' and R", independently of one another, representing a protective group:

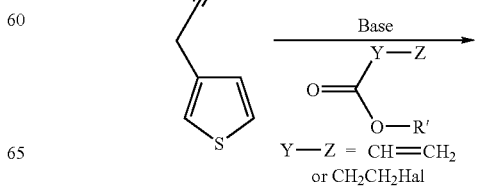

Y—Z = CH=CH₂
or CH₂CH₂Hal

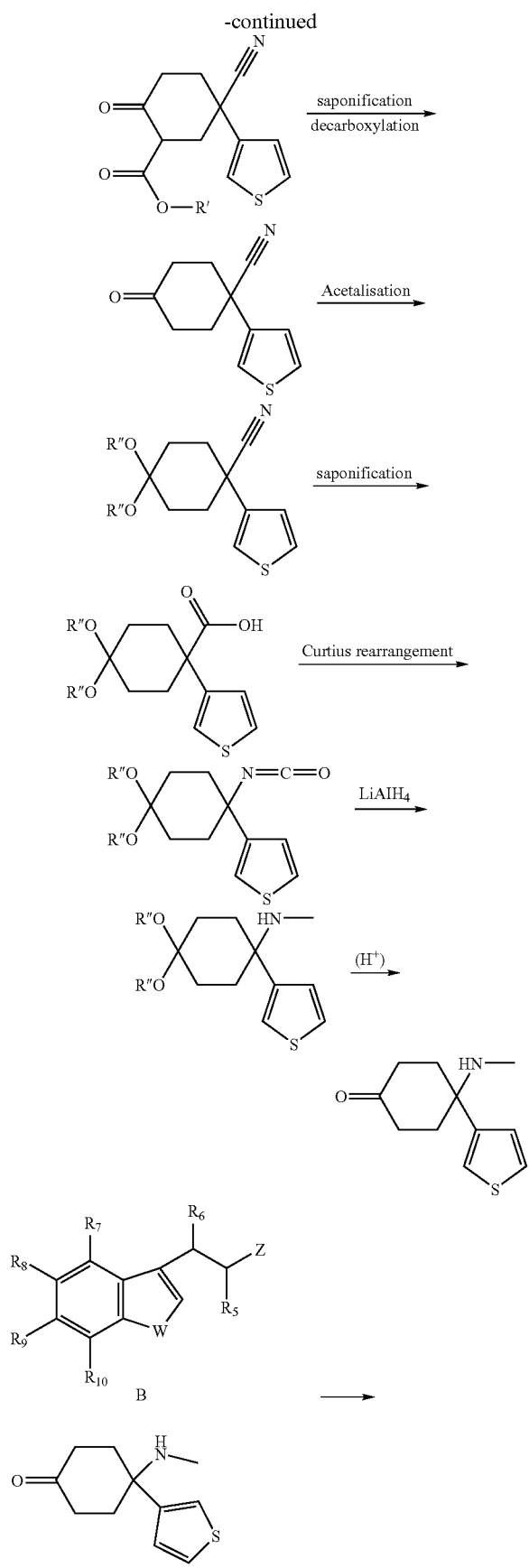

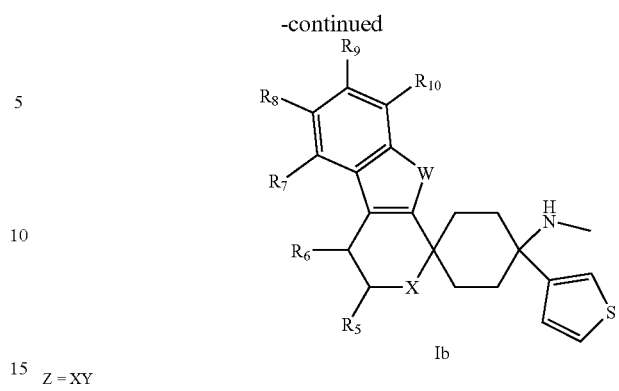

Z = XY
Y = H, SiMe₃

With this process, a leaving group such as, for example, a halogen, preferably bromine, is introduced into the methyl group of the 3-methylthiophene by methods known to a person skilled in the art, for example by bromination with N-bromosuccinimide in an inert solvent such as, for example, benzene, with addition of an initiator such as, for example, benzoyl peroxide and optionally with heating.

The resulting product, for example 3-bromomethyl-thiophene, is converted into the corresponding nitrile using a cyanide source such as, for example, sodium cyanide, for example in the presence of a quaternary ammonium salt such as, for example, tetrabutyl ammonium bromide, optionally with heating.

The thiophen-3-yl-acetonitrile obtained is reacted in the presence of an excess of an acrylic ester or a 3-bromopropionic acid ester, preferably with about 2.3 mole equivalents of 3-bromopropionic acid ethylester, and in the presence of a base, for example sodium amide, in an aprotic solvent, for example toluene, and can optionally be heated.

The resultant 5-cyano-2-oxo-5-thiophen-3-yl-cyclohexane carboxylic acid esters may be hydrolyzed and decarboxylated by processes known in the art, for example, by heating in a mixture of concentrated hydrochloric acid and glacial acetic acid under reflux.

The resultant keto group of the 4-oxo-1-thiophen-3-yl-cyclohexane carbonitrile may be provided with a protective group by processes known in the art, for example by acetalization, particularly preferably by conversion into the ethylene dioxy protective group, more particularly preferably by heating the ketone in toluene in the presence of ethylene glycol and an acidic catalyst, for example paratoluene sulfonic acid with heating, preferably under reflux.

The resultant 8-thiophen-3-yl-1,4-dioxa-spiro[4.5]decane-8-carbonitrile may be converted into the corresponding carboxylic acid by saponification of the nitrile group by processes known in the art, for example in a basic medium, preferably with sodium hydroxide in ethyleneglycol under reflux.

The resultant 8-thiophen-3-yl-1,4-dioxa-spiro[4.5]decane-8-carboxcylic acid may be converted into the corresponding isocyanate by processes known in the art, preferably by reactions which take place in the manner of a Curtius rearrangement. The carboxylic acid is preferably converted into the isocyanate with azidophosphoric acid diphenylester in the presence of triethylamine in anisole with heating under reflux.

The resultant 8-isocyanato-8-thiophen-3-yl-1,4-dioxa-spiro[4.5]decane may be converted into the corresponding methylamino compound, for example with lithium aluminium hydride in an aprotic solvent, preferably tetrahydrofuran. The resultant methyl-(8-thiophen-3-yl-1,4-dioxaspiro[4.5]dec-8-yl)amine may be deprotected by acid catalysis to the 4-methylamino-4-thiophen-3-yl-cyclohexanone and then reacted, for example with compounds of general formula B, to spirocyclic cyclohexane compounds.

EXAMPLES

The following examples are intended to illustrate the invention in further detail, without limiting its scope. The yields of compounds produced have not been optimized. All temperatures are uncorrected.

The term "ether" denotes diethylether, "EE" ethylacetate, "DCM" dichloromethane, "DMF" dimethylformamide, "DMSO" dimethyl sulfoxide and "THF" tetrahydofuran. The term "equivalent" denotes equivalent of amount of substance, "mp" melting point or melting range, "decomp." decomposition, "RT" room temperature, "abs." absolute (anhydrous), "rac." racemic, "conc." concentrated, "min" minutes, "h" hours, "d" days, "vol. %" percentage by volume, "m %" percentage by mass and "M" is a concentration in moles per liter.

Silica gel 60 (0.040-0.063 mm) from E. Merck, Darmstadt was used as the stationary phase for column chromatography. Thin-layer chromatography tests were carried out using HPTLC chromatoplates, silica gel 60 F 254, from E. Merck, Darmstadt. The mixing ratios of mobile solvent for chromatographic tests are always given in volume/volume.

Example 1

1,1-[3-dimethylamino-3-(pyridin-2-yl)pentamethylene]-3,4-dihydro-1H-2,9-diazafluorene, Diastereoisomer Mixture 4-dimethylamino-4-pyridin-2-yl cyclohexanone (4.37 g, 20 mmole) and 2-(1H-indol-3-yl)-ethylamine ("Tryptamine", 3.2 g, 20 mmole) were dissolved in dry MeOH (200 ml) under argon. MeOH was distilled off after a reaction time of 24 hours, the yellow oily residue was suspended in 1,2-dichloroethane (200 ml), trifluoroacetic acid (20 ml) was added and the mixture was stirred for 2 h at room temperature. The mixture was worked up by dilution with water (100 ml) and adjusted to pH 11 using NaOH (5 mol/l). After addition of EE (50 ml), a white solid precipitated during stirring and was suction-filtered over a frit. The solid was washed with water (3×25 ml) and dried under vacuum. 1,1-[3-dimethylamino-3-(pyridin-2-yl)pentamethylene]-3,4-dihydro-1H-2,9-diazafluorene was obtained as a diastereoisomer mixture (4.9 g white solid, mp 122-125° C.).

Example 2

2-acetyl-1,1-[3-dimethylamino-3-(pyridin-2-yl)pentamethylene]-3,4-dihydro-1H-2,9-diazafluorene The 1,1-[3-dimethylamino-3-(pyridin-2-yl)pentamethylene]-3,4-dihydro-1H-2,9-diazafluorene (200 mg, 0.56 mmole) obtained in Example 1 was dissolved in pyridine (5 ml), acetanhydride was added dropwise (484 µl, 5.6 mmole) and the mixture was stirred for 5 days at room temperature. To work up the mixture, pyridine was distilled off in a rotary evaporator, the residue was diluted with water (10 ml), adjusted to pH 11 using 5M NaOH and extracted with EE (3×10 ml). A solid precipitated from the combined organic extracts and was suction-filtered and dried. 160 mg of a diastereoisomer-pure white solid were obtained. 150 mg (0.37 mmole) thereof were dissolved in hot ethanol (10 ml) and were reacted with a similarly hot solution of citric acid (72 mg, 0.37 mmole) in ethanol (1 ml). The mixture was cooled to approx. 5° C. then left to stand for 4 hours, and was subsequently concentrated to dryness. The citrate of 2-acetyl-1,1-[3-dimethylamino-3-(pyridin-2-yl)pentamethylene]-3,4-dihydro-1H-2,9-diazafluorene was thus obtained in a yield of 222 mg (white foam, mp 108-112° C.).

Example 3

1,1-[3-dimethylamino-3-(pyridin-2-yl)pentamethylene]-3,4-dihydro-1H-2-oxa-9-thiafluorene Citrate 4-dimethylamino-4-pyridin-2-yl cyclohexanone (218 mg, 1 mmole) and 2-benzo[b]thiophen-2-ylethanol (178 mg, 1 mmole) were dissolved in abs. DCM (5 ml) under argon, methane sulfonic acid (3 ml) was added, and the mixture was stirred for 3 days at room temperature. The reaction mixture was worked up by addition of ice (5 g) and water (30 ml). After neutralization with sodium-hydrogen carbonate (4.4 g, 52 mmole) and addition of 5M NaOH (1 ml), DCM (10 ml) was added, the organic phase was separated and the aqueous phase was extracted with DCM (2×30 ml). The combined organic phases were dried, then concentrated, and the residue (375 mg) was separated by chromatography over silica gel (45 g, Eluant: EE/methanol 10:1 followed by 4:1 then methanol). The crude product was obtained as a white solid in a yield of 143 mg (0.377 mmole) (mp 155-168° C.), was dissolved in ethanol (10 ml) at 50° C., was reacted with citric acid (72 mg, 0.377 mmole), dissolved in warm ethanol (3 ml), stirred for 2 hours at room temperature and concentrated to 5 ml. The precipitated solid was suction-filtered and washed with ethanol (2×1 ml). 1,1-[3-dimethylamino-3-(pyridin-2-yl)pentamethylene]-3,4-dihydro-1H-2-oxa-9-thiafluorene citrate was obtained in a yield of 179 mg (white solid, mp 189-191° C.).

Example 4

1,1-[3-dimethylamino-3-(pyridin-2-yl)pentamethylene]-1,3,4,9-tetrahydropyrano-[3,4-b]indole hemicitrate, Non-Polar Diastereoisomer 4-dimethylamino-4-pyridin-2-yl cyclohexanone (654 mg, 3 mmole) and 2-(1H-indol-3-yl)ethanol ("Tryptophol", 483 mg, 3 mmole) were placed in DCM (50 ml), were added to methane sulfonic acid (400 µl, 6.2 mmole) within 3 minutes and stirred for 70 hours at room temperature. For working up, the reaction mixture was reacted with 2M NaOH (15 ml), was stirred for 20 min, the organic phase was separated and the remaining aqueous phase was shaken with dichloromethane (3×20 ml). The combined organic phases were washed with water (2×30 ml), dried, filtered and concentrated. The residue obtained was subjected to chromatography over silica gel (60 g, EE/ethanol 2:1), and the base of the non-polar diastereoisomer of the target product was obtained in a yield of 123 mg. 108 mg (0.3 mmole) thereof were dissolved in hot ethanol (15 ml), reacted with a similarly hot ethanolic citric acid solution (58 mg, 0.3 mmole in 1 ml) and the mixture left at 5° C. for 12 hours. The resultant solid was suction-filtered. The hemicitrate of the non-polar diastereoisomer of 1,1-[3-dimethylamino-3-(pyridin-2-yl)pentamethylene]-1,3,4,9-tetrahydropyrano-[3,4-b]indole was thus obtained in a yield of 79 mg (white solid, mp 255-260° C.).

Example 5

1,1-[3,dimethylamino-3-(pyridin-2-yl)pentamethylene]-1,3,4,9-tetrahydropyrano-[3,4-b]indole citrate, Polar Diastereoisomer As described in Example 4, 415 mg of the polar diastereoisomer of 1,1-[3-dimethylamino-3-(pyridin-2-yl)pentamethylene]-1,3,4,9-tetrahydropyrano-[3,4-b]indole were also obtained. 400 mg (1.1 mmole) thereof were dissolved in hot ethanol (12 ml) and hot ethanolic citric acid solution (total 211 mg, 1.1 mmole in 2 ml) was added. The mixture was left for 2 hours at 5° C. and then concentrated to dryness. The citrate of the polar diastereoisomer of 1,1-[3-dimethylamino-3-(pyridin-2-yl)pentamethylene]-1,3,4,9-tetrahydropyrano-[3,4-b]indole was thus obtained in a yield of 612 mg (white vitreous solid, mp 96-100° C.).

Example 6

1,1-[3-dimethylamino-3-(2-thienyl)pentamethylene]-1,3,4,9-tetrahydro-pyrano[3,4-b]indole Dimethanesulfonate and

Example 7

1,1-[3-dimethylamino-3-(2-thienyl)pentamethylene]-1,3,4,9-tetrahydro-pyrano[3,4-b]indole Citrate 4-dimethylamino-4-(2-thienyl)-cyclohexanone (223 mg, 1 mmole) and 2-(1H-indol-3-yl)ethanol (161 mg, 1 mmole) were dissolved in absolute DCM, and methanesulfonic acid (0.071 ml, 1.1 mmole) was added. The mixture was stirred for 16 hours at room temperature. The polar diastereomer of 1,1-[3-dimethylamino-3-(2-thienyl)pentamethylene]-1,3,4,9-tetrahydro-pyrano[3,4-b]indole precipitated as dimethanesulfonate (Example 6). The light grey solid was obtained in a yield of 25% (117 mg; mp 132° C.).

The filtrate was reacted with 1M NaOH (20 ml) and stirred for 16 hours at room temperature. The organic phase was separated, the aqueous phase extracted with DCM, and the combined organic phases were concentrated. A mixture of substances was obtained and was separated by chromatography [silica gel G (20 g); EE/methanol 8:1]. The nonpolar diastereoisomer of 1,1-[3-dimethylamino-3-(2-thienyl)pentamethylene]-1,3,4,9-tetrahydro-pyrano[3,4-b]indole was obtained in a yield of 54% (196 mg, mp 235-238° C.), and the polar diastereoisomer in a yield of 10% (38 mg).

To produce the citrate, the non-polar diastereoisomer of 1,1-[3-dimethylamino-3-(2-thienyl)pentamethylene]-1,3,4,9-tetrahydro-pyrano[3,4-b]indole (170 mg, 0.46 mmole) was dissolved in ethanol (50 ml) with heating and reacted with citric acid 98 mg, 0.51 mmole) in ethanol (5 ml). The mixture was stirred for 1 hour at room temperature. The citrate (Example 7) was obtained as a colorless compound in a yield of 60% (153 mg, mp 222-225° C.).

Example 8

1,1-[3-dimethylamino-3-(3-thienyl)pentamethylene]-1,3,4,9-tetrahydro-pyrano[3,4-b]indole Hemicitrate and

Example 9

1,1-[3-dimethylamino-3-(3-thienyl)pentamethylene]-1,3,4,9-tetrahydro-pyrano[3,4-b]indole Citrate 4-dimethylamino-4-(3-thienyl)-cyclohexanone (223 mg, 1 mmole) and 2-(1H-indol-3-yl)ethanol (161 mg, 1 mmole) were dissolved in absolute DCM (50 ml) and reacted with methanesulfonate acid (0.13 ml, 2.0 mmole). The mixture was stirred for 2 days at room temperature. A proportion of the polar diastereomer of 1,1-[3-dimethylamino-3-(3-thienyl)pentamethylene]-1,3,4,9-tetrahydro-pyrano[3,4-b]indole precipitated as the methanesulfonate. The solid was suction-filtered, washed with DCM and obtained in a yield of 12% (55 mg). The filtrate was reacted with 0.5 M NaOH (20 ml) and stirred for 2 hours at room temperature. The non-polar diastereoisomer of 1,1-[3-dimethylamino-3-(3-thienyl)pentamethylene]-1,3,4,9-tetrahydro-pyrano[3,4-b] indole precipitated as a colorless solid and was obtained in a yield of 38% (138 mg) with a mp of 291-294° C. after filtration. The organic phase of the filtrate was separated, and the aqueous phase was extracted with DCM (2×20 ml). The combined organic phases yielded a diastereoisomer mixture (184 mg, 50%). After reaction with methanol (10 ml), only the polar diastereoisomer of 1,1-[3-dimethylamino-3-(3-thienyl)pentamethylene]-1,3,4,9-tetrahydro-pyrano[3,4-b] indole (45 mg, 12%, fp 235-238° C.) was dissolved and the residue was the nonpolar diastereoisomer.

To produce the citrate, the non-polar diastereoisomer of 1,1-[3-dimethylamino-3-(3-thienyl)pentamethylene]-1,3,4,9-tetrahydro-pyrano[3,4-b]indole (111 mg, 0.3 mmole) was dissolved in ethanol (35 ml) with heating at 50° C. and suspended and reacted with citric acid (60 mg, 0.31 mmole) in ethanol (5 ml). The mixture was stirred for 16 hours at room temperature. The precipitated hemicitrate (Example 8) was suction-filtered and washed with ethanol (2×5 ml). The colorless compound was obtained in a yield of 79% (110 mg, mp 246-250° C.).

The polar diastereoisomer (81 mg, 0.22 mmole) was dissolved in ethanol (20 ml), reacted with citric acid (46 mg, 0.24 mmole) in ethanol (3 ml) and stirred for 16 hours at room temperature. The clear mixture was concentrated to 3 ml, reacted with diethylether (40 ml) and stirred for 15 min at room temperature. The polar citrate precipitated as a colorless solid in a yield of 63% (77 mg; mp 245-248° C.).

Example 10

1,1-[3-dimethylamino-3-(2-thienyl)pentamethylene]-1,3,4,9-tetrahydro-pyrano[3,4-b]-6-fluoroindole Hemicitrate and

Example 11

1,1-[3-dimethylamino-3-(2-thienyl)pentamethylene]-1,3,4,9-tetrahydro-pyrano[3,4-b]-6-fluoroindole Citrate 4-dimethylamino-4-(2-thienyl)-cyclohexanone (223 mg, 1 mmole) and 5-fluoro-2(1H-indol-3-yl)ethanol (179 mg, 1 mmole) were placed in absolute DCM (50 ml) and reacted with methanesulfonic acid (0.13 ml, 2.0 mmole). The mixture was stirred for 20 hours at room temperature and then reacted with 0.5 M NaOH (20 ml) and stirred for 2 hours at room temperature. The organic phase was separated, and the aqueous phase was extracted with DCM. A diastereoisomer mixture of 1,1-[3-dimethylamino-3-(2-thienyl)pentamethylene]-1,3,4,9-tetrahydro-pyrano[3,4-b]-6-fluoroindole (382 mg) was obtained from the organic phases. This was recrystallized from propan-2-ol (70 ml). The nonpolar diastereoisomer precipitated (165 mg, 43%). A diastereoisomer mixture was isolated from the filtrate after evaporation (211 mg). After chromatographic separation of this mixture [silica gel G (40 g); EE/cyclohexane 1:1 (400 ml), EE (400 ml), EE/methanol 4:1 (300 ml)], the nonpolar diastereoisomer (67 mg, 17%, mp 225-230° C.) and the polar diastereoisomer (110 mg, 29%, mp 197-202° C.) were obtained as colorless solids.

To produce the citrate, the nonpolar diastereoisomer (165 mg, 0.43 mmole) was suspended in ethanol (50 ml) with heating and reacted with citric acid (93 mg, 0.48 mmole) in ethanol (5 ml). The mixture was stirred for 30 min at 50° C. and for 16 hours at room temperature. The hemicitrate was suction-filtered and washed with ethanol. The colorless compound was obtained in a yield of 54% (111 mg; mp 199-201° C.) (Example 10).

The polar diastereoisomer (91 mg, 0.236 mmole) was dissolved in ethanol (15 ml) at 40° C., reacted with citric acid (52 mg, 0.27 mmole) in ethanol (5 ml) and stirred for 2 hours at room temperature. The solution was concentrated to 3 ml, reacted with ether (40 ml) and stirred for 16 hours at room temperature. The polar hemicitrate precipitated as a colorless solid in a yield of 93% (106 mg; mp 137-140° C.) (Example 11).

Example 12

1,1-[3-dimethylamino-3-(3-thienyl)pentamethylene]-1,3,4,9-tetrahydro-pyrano[3,4-b]-6-fluoroindole Dimethanesulfonate and Example 13

1,1-[3-dimethylamino-3-(3-thienyl)pentamethylene]-1,3,4,9-tetrahydro-pyrano[3,4-b]-6-fluoroindole Hemicitrate 4-dimethylamino-4-(3-thienyl)-cyclohexanone (446.6 mg, 2 mmole) and 5-fluoro-2(1H-indol-3-yl)ethanol (394.4 mg, 2 mmole) were dissolved in absolute 1.2 dichloroethane (30 ml) and reacted with methanesulfonic acid (0.13 ml, 2.0 mmole). The mixture was stirred for 20 hours at room temperature. The precipitated methanesulfonate of the polar diastereoisomer was then suction-filtered and washed with 1,2-dichlorethane. The light grey solid was obtained in a yield of 76% (733 mg; mp 143-145° C.) (Example 12).

The filtrate was reacted with 1 M NaOH (30 ml) and stirred for 2 hours at room temperature. The nonpolar diastereoisomer precipitated as a colorless solid and was obtained in a yield of 8% (58.5 mg). The phases of the filtrate were separated, and the aqueous phase was extracted with DCM. The combined organic phases contained a diastereoisomer mixture (300.3 mg).

To produce the citrate, the diastereoisomer mixture (126 mg, 0.33 mmole) was suspended in ethanol (100 ml) with heating at 50° C. and was reacted with citric acid (69.2 mg, 0.36 mmole) in ethanol (5 ml). The mixture was stirred for 2 hours at room temperature and stored overnight at 10° C. The precipitated hemicitrate of the nonpolar diastereoisomer was suction-filtered. The colorless compound was obtained in a yield of 60% (94 mg; mp 227-229° C.) (Example 13).

Example 14

1,1-[3-methylamino-3-(2-thienyl)pentamethylene]-1,3,4,9-tetrahydro-pyrano[3,4-b]indole Citrate 4-methylamino-4-thiophen-2-yl-cyclohexanone (418.6 mg, 2.0 mmole) and 2-(1H-indol-3-yl)-ethanol (322.4 mg, 2.0 mmole) were dissolved in 50 ml DCM and quickly reacted with trifluoromethane sulfonic acid (0.18 ml, 2.03 mmole). After stirring for 20 hours at room temperature, the mixture was stirred for 20 min with 20 ml 2 M NaOH. The organic phase was separated, and the aqueous phase extracted with DCM. The combined organic phases were concentrated to dryness under vacuum, and the residue was suspended in 25 ml methanol. The colorless solid was suction-filtered, and 1,1-[3-methylamino-3-(2-thienyl)pentamethylene]-1,3,4,9-tetrahydro-pyrano[3,4-b]indole was thus obtained in a yield of 363 mg (51%).

To produce the citrate, 1,1-[3-methylamino-3-(2-thienyl)pentamethylene]-1,3,4,9-tetrahydro-pyrano[3,4-b]indole (352 mg, 1.0 mmole) was dissolved in hot ethanol (30 ml) and reacted with citric acid (200 mg, 1.04 mmole) in hot ethanol (5 ml). The mixture was left to stand for 15 hours at 5° C. The precipitated citrate was suction-filtered and obtained as a colorless compound in a yield of 69% (377 mg; mp 201-203° C.) (Example 14).

Example 15

1,1-[3-methylamino-3-(2-thienyl)pentamethylene]-1,3,4,9-tetrahydro-pyrano[3,4-b]-6-fluoroindole Citrate 4-methylamino-4-thiophen-2-yl-cyclohexanone (418.6 mg, 2.0 mmole) and 2-(5-fluoro-1H-indol-3-yl)-ethanol (358.3 mg, 2.0 mmole) were dissolved in 50 ml DCM and quickly reacted with trifluoromethane sulfonic acid (0.18 ml, 2.03 mmole). After stirring for 20 hours at room temperature, the mixture was stirred for 20 min with 20 ml 2 M NaOH. The organic phase was separated, and the aqueous phase was extracted with DCM. The combined organic phases were concentrated to dryness under vacuum, and the residue was suspended in methanol. The colorless solid was suction-filtered, and 1,1-[3-methylamino-3-(2-thienyl)pentamethylene]-1,3,4,9-tetrahydro-pyrano[3,4-b]fluoroindole was thus obtained in a yield of 697 mg (94%).

To produce the citrate, the spirocyclic ether (680 mg, 1.84 mmole) was dissolved in hot ethanol (50 ml) and reacted with citric acid (384 mg, 2.0 mmole) in hot ethanol (10 ml). The mixture was left to stand for 15 hours at 5° C. The precipitated citrate was suction-filtered and obtained as a colorless compound in a yield of 67% (694 mg; mp 207-209° C.) (Example 15).

3-bromomethyl-thiophene

N-bromosuccinimide (35.6 mg; 0.20 mole) and benzoylperoxide (0.4 g; 0.0013 mole) were added batchwise to a mixture of 3-methylthiophene (22 g; 0.203 mole) and benzoylperoxide (0.4 g; 0.0013 mole) in dry benzene over 90 min at 90° C. On completion of the reaction (reaction monitored by thin layer chromatography), the mixture was cooled to 0° C. and filtered. The filtrate was concentrated under vacuum. 34 g 3-bromomethyl-thiophene (reddish brown liquid) were obtained.

Thiophen-3-yl-acetonitrile

Sodium cyanide (12.03 g; 0.25 mole) and catalytic quantities of tetra-n-butyl ammonium bromide were added to a mixture of 3-bromomethyl-thiophene (29 g; 0.16 mole) in dichloromethane (175 ml) and water (50 ml). The reaction mixture was stirred under reflux. On completion of the reaction (reaction monitored by thin layer chromatography), the organic phase was separated, washed with water (3×500 ml), dried (sodium sulfate) and concentrated under vacuum. Purification by column chromatography (silica gel, 3% ethyl acetate in n-hexane) yielded 9 g thiophen-3-yl-acetronitrile (44%; reddish brown liquid).

5-cyano-2-oxo-5-thiophen-3-yl-cyclohexanecarboxycylic Acid Ethylester 3-bromopropionic acid ethylester (96.14 g; 0.53 mol) were added to thiophen-3-yl-acetonitrile (27.5 g; 0.22 mol) dissolved in 350 ml toluene. Sodium amide (74.03 g; 1.9 mol) was then added batchwise within 1H at 0 to 10° C. The reaction mixture was then stirred for about 1 h under reflux. On completion of the reaction (reaction control by thin layer chromatography), excess sodium amide was decomposed with acetic acid/water (500 ml; 2:1) at 0 to 5° C. The organic phase was separated and neutralised with sodium hydrogen carbonate solution (300 ml), dried (sodium sulfate) and concentrated under vacuum. 40 g 5-cyano-2-oxo-5-thiophen-3-yl-cyclohexanecarboxycylic acid ethylester (yellow liquid) were obtained.

4-oxo-1-thiophen-3-yl-cyclohexanecarbonitrile 5-cyano-2-oxo-5-thiophen-3-yl-cyclohexanecarboxylic acid ethylester (40 g; 0.14 mole) dissolved in a mixture of concentrated hydrochloric acid (200 ml) and glacial acetic acid (400 ml) was heated with stirring for about 4 hours to reflux. On completion of the reaction (reaction monitored by thin layer chromatography), water (100 ml) was added and neutralized with aqueous sodium hydroxide solution (200 ml) and extracted with ethylacetate (2×400 ml). The organic phase was washed with sodium hydrogen carbonate solution (200 ml) and water (100 ml), dried (sodium sulfate) and concentrated under vacuum. Purification by column chromatography (silica gel, 25% ethylacetate in n-hexane) yielded 12.5 g 4-oxo-1-thiophen-3-yl-cyclohexanecarbonitrile (42%; pale yellow solid).

8-thiophen-3-yl-1,4-dioxa-spiro[4.5]decane-8-carbonitrile

Catalytic quantities of para-toluene sulfonic acid and ethyleneglycol (13.3 g: 0.21 mole) were added to 4-oxo-1-thiophen-3-yl-cyclohexanecarbonitrile (22 g; 0.107 mole) dissolved in toluene (500 ml). The reaction mixture was stirred for about 2 hours under reflux. On completion of the reaction (reaction monitored by thin layer chromatography), the toluene phase was separated, washed with sodium hydrogen carbonate solution (200 ml), dried (sodium sulfate) and concentrated under vacuum. 25 g 8-thiophen-3-yl-1,4-dioxa-spiro[4.5]decane-8-carbonitrile (95%; colorless solid) were obtained.

8-thiophen-3-yl-1,4-dioxa-spiro[4.5]decane-8-carboxylic Acid

Potassium hydroxide (28 g; 0.5 mole) was added to 8-thiophen-3-yl-1,4-dioxa-spiro[4.5]decane-8-carbonitrile (25 g; 0.095 mole) dissolved in ethylene glycol (226 ml). The reaction mixture was stirred for about 22 hours under reflux. On completion of the reaction (reaction monitored by thin layer chromatography), the reaction mixture was adjusted to a pH of about 1 with dilute hydrochloric acid. The resultant precipitate was filtered and dried. 15 g of 8-thiophen-3-yl-1,4-dioxa-spiro[4.5]decane-8-carboxylic acid (55%; pale yellow solid) were obtained.

8-isocyanato-8-thiophen-3-yl-1,4-dioxa-spiro[4.5]decane

Azidophosphoric acid diphenyl ester (15.4 g; 56 mmole) and triethylamine (5.66 g; 55 mmole) were added to 8-thiophen-3-yl-1,4-dioxa-spiro[4.5]decane-8-carboxylic acid (15 g; 56 mmole) dissolved in anisole (160 ml). The reaction mixture was heated for 2 hours to 90 to 100° C. On completion of the reaction (reaction monitored by thin layer chromatography), the mixture was purified by column chromatography (silica gel, 10% ethyl acetate in n-hexane). 6 g of 8-isocyanato-8-thiophen-3-yl-1,4-dioxa-spiro[4.5]decane were obtained (41%; colorless liquid).

Methyl-(8-thiophen-3-yl-1,4-dioxa-spiro[4.5]dec-8-yl)-amine

Lithium aluminium hydride (1.7 g) was added batchwise to 8-isocyanato-8-thiophen-3-yl-1,4-dioxa-spiro[4.5]decane (6 g; 22.6 mmole) dissolved in dry THF (70 ml) at 0 to 5° C. The reaction mixture was stirred for about 1.5 hours under reflux. On completion of the reaction (reaction monitored by thin layer chromatography), excess lithium aluminium hydride was destroyed with saturated aqueous sodium sulfate solution (20 ml). The resultant precipitate was filtered out over Celite. The filtrate was concentrated and extracted with ethyl acetate (3×100 ml). The organic phase was separated, dried (sodium sulfate) and concentrated under vacuum. Purification by column chromatography (silica gel, 50% ethyl acetate in n-hexane) yielded 2.5 g methyl-(8-thiophen-3-yl-1,4-dioxa-spiro[4.5]dec-8-yl)-amine (43%; white low-melting solid).

Example 16

1,1-[3-methylamino-3-(3-thienyl)pentamethylene]-1,3,4,9-tetrahydro-pyrano[3,4-b]indole Citrate Example 16 was carried out similarly to Example 14 from 4-methylamino-4-thiophen-3-yl-cyclohexane and 2-(1H-indol-3-yl)-ethanol.

Example 17

1,1-[3-methylamino-3-(3-thienyl)pentamethylene]-1,3,4,9-tetrahydro-pyrano[3,4-b]-6-fluoroindole Citrate Example 17 was carried out similarly to Example 15 from 4-methylamino-4-thiophen-3-yl-cyclohexane and 2-(5-fluoro-1H-indol-3-yl)-ethanol.

Biological Data

Measurement of ORL1 Binding

The 4-aminocyclohexanol compounds of formula I were investigated in a receptor binding assay with $^3$H-nociceptin/orphanin FQ with membranes of recombinant CHO-ORL1 cells. This test was conducted in accordance with the method described by Ardati et al. (Mol. Pharmacol., 51, 1997, p. 816-824). The concentration of $^3$H-nociceptin/orphanin FQ in these experiments was 0.5 nM. The binding assays were carried out with 20 μg amounts of membrane protein per 200 μl batch in 50 mM Hepes, pH 7.4, 10 mM $MgCl_2$ and 1 mM EDTA. The binding to the ORL1 receptor was determined using respective 1 mg amounts of WGA-SPA beads (Amersham-Pharmacia, Freiburg), by incubation of the batch for one hour at room temperature and subsequent measurement in a Trilux scintillation counter (Wallac, Finland). The affinity is given as the $K_i$ value.

Measurement of the μ-Bond

The receptor affinity for the human g-opiate receptor was determined in a homogeneous mixture in microtitre plates. For this purpose, dilution series of the respective substituted spirocyclic cyclohexane compound to be tested were incubated with a receptor membrane preparation (15-40 μg protein per 250 μl incubation mixture) of CHO-K1 cells, which express the human μ-opiate receptor (RB-HOM receptor membrane preparation from NEN, Zaventem, Belgium) in the presence of 1 umole/liter of the radioactive ligand [$^3$H]-Naloxon (NET719, NEN, Zaventem, Belgium) and 1 mg WGA-SPA-beads (Wheat germ agglutinin SPA beads from Amersham/Pharmacia, Freiburg, Germany) in a total volume of 250 μl for 90 minutes at room temperature. 50 mmole/liter tris-HCl were added as incubation buffer with 0.05% by weight sodium azide and 0.06% by weight bovine serum albumin. 25 μmole/liter naloxon were also added to determine the non-specific bond. At the end of the 90 minute incubation period, the microtitre plates were centrifuged off for 20 minutes at 1000 g, and the radioactivity was measured in a β-counter (Microbeta-Trilux, PerkinElmer Wallac, Freiburg, Germany). The percentage displacement of the radioactive ligand from its bond with the human μ-opiate receptor at a concentration of the test substances of 1 μmole/liter was determined and given as a percentage inhibition (% inhibition) of the specific bond. $IC_{50}$ inhibition concentrations, which bring about a 50% displacement of the radioactive ligand, were in some cases calculated by taking as a basis the percentage displacement by various concentrations of the compounds of general formula I to be tested. Ki values for the test substances were obtained by conversion using the Cheng-Prusoff equation.

| Example | ORL1 Ki (nM) or % inhibition | ORμ_Nal Ki (nM) or % inhibition |
|---|---|---|
| 1 | 1.60 | 2.80 |
| 3 | 49% | 140.00 |
| 4 | 0.49 | 0.08 |
| 5 | 29% | 210.00 |
| 6 | 37% | 47% |
| 7 | 0.56 | 0.27 |
| 8 | 0.26 | 0.12 |
| 10 | 0.66 | 0.09 |
| 11 | 41% | 53% |
| 12 | 59% | 150.00 |
| 13 | 0.61 | 0.08 |

Analgesia Test in the Tail Flick Test in the Mouse

The mice were each placed individually into a test cage, and the base of the tail was exposed to the focused heat ray of an electric lamp (tail-flick type 50/08/1.bc, Labtec, Dr. Hess). The intensity of the lamp was adjusted so that the time from switching on of the lamp to the sudden twitching away of the tail (latency of pain) in untreated mice was from 3 to 5 seconds. Before administration of the solutions comprising the compound according to the invention or of the particular comparison solutions, the mice were pretested twice over the course of five minutes, and the mean of those measurements was calculated as the pre-test mean.

The solutions of the compound of the general formula I according to the invention and the comparison solutions were then administered intravenously. Pain measurement was carried out in each case 10, 20, 40 and 60 minutes following the intravenous administration. The analgesic activity was determined as the increase in the latency of pain (% of the maximum possible antinociceptive effect) according to the following formula:

$$[(T_1-T_0)/(T_2-T_0)] \times 100$$

where time $T_0$ is the latency before administration, time $T_1$ is the latency after administration of the active ingredient combination and time $T_2$ is the maximum exposure time (12 seconds).

| Example | Tail Flick (mouse, i.v.) $ED_{50}$ |
|---|---|
| 7 | 3.5 μg/kg |
| 10 | 0.028 mg/kg |
| 13 | 0.027 mg/kg |

Example 7 induces muscle relaxation and anesthesia in mice at higher doses. Example 7 shows reduced place preference compared to selective μ-opioids such as morphine (for an explanation of place preference see Tzschentke, T. M., 1998 Prog. Neurobiol, 56:613-672).

Mouse Jumping Test

The mouse jumping test is a screening method to estimate the physical dependence capacity of analgesics (see Saelens J K, Granat F R, Sawyer W K, Arch Int Pharmacodyn Ther. 1971 Apr; 190(2):213-8).

Experimental Animals

The experiment was carried out in male NMRI-mice (weighing 25-35 g) supplied by a commercial breeder (IFFA CREDO, Brussels, Belgium). The animals were housed under standardizd conditions: light/dark cycle (06.00-18.00 h light, 18.00-06.00 h dark); room temperature 20-24° C.; relative air humidity 45-70%; 15 air changes per hour, air movement <0.2 m/sec. The animals had free access to standard laboratory food (ssniff R/M-Haltung, ssniff Spezialdiäten GmbH, Soest, Germany) and tap water. Both were withdrawn during the test. All mice were used only once. There were at least five days between delivery of the animals and the test day.

Methods:

Administrations (i.p.) were made in a volume of 10.0 ml/kg. The physical dependence potential of the test compounds were investigated according to the method of Saelens et al (1971). Administrations were made repeatedly over two days during which the mice received 7 intraperitoneal injections. Five were given on the first day at 9.00, 10.00, 11.00 a.m. and 13.00 and 15.00 p.m.. On the second day of experiment the substances were given at 9.00 and 11.00 a.m. The first three administrations were given in an escalating dose scheme. The remaining doses were maintained at the level of the third dose. Withdrawal was precipitated 2 hours after the pre-treatment by i.p. administration of 30 mg/kg naloxone. The animals were placed in glass jars (height 25 cm, diameter 15 cm) immediately after administration of naloxone and the number of jumps (all 4 paws off the bottom surface) were recorded over 15 min in 5-min observation periods.

Statistical Analysis of the Results and Evaluation

Withdrawal was quantified from the number of jumps 0-10 min after administration of naloxone. The number of animals with a jumping frequency of more than 10 jumps/10 min was determined for each dose group and the mean jumping frequency in these animals was calculated. Groups of 12 mice were used for each dose.

BRIEF DESCRIPTION OF THE DRAWING

The FIGURE shows test results from Example 7.

Example 7

Jumping is completely suppressed.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A spirocyclic cyclohexane compound corresponding to formula I

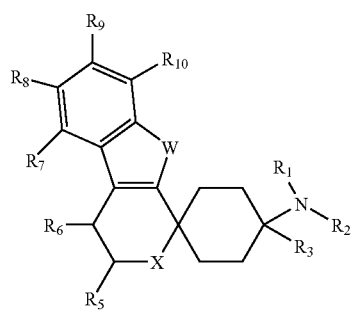

wherein
$R^1$ and $R^2$ independently represent H; CHO; respectively saturated or unsaturated, branched or unbranched, singly or multiply substituted or unsubstituted $C_{1-5}$ alkyl; respectively saturated or unsaturated, singly or multiply substituted or unsubstituted $C_{3-8}$ cycloalkyl; or respectively singly or multiply substituted or unsubstituted aryl, $C_{3-8}$ cycloalkyl or heteroaryl bound by $C_{1-3}$ alkyl; or $R^1$ and $R^2$ together represent $CH_2CH_2OCH_2CH_2$, $CH_2CH_2NR^{11}CH_2CH_2$ or $(CH_2)_{3-6}$;
  wherein $R^{11}$ represents H; respectively saturated or unsaturated, branched or unbranched, singly or multiply substituted or unsubstituted $C_{1-5}$ alkyl; respectively saturated or unsaturated, singly or multiply substituted or unsubstituted $C_{3-8}$ cycloalkyl; respectively singly or multiply substituted or unsubstituted aryl or heteroaryl; or respectively singly or multiply substituted or unsubstituted aryl, $C_{3-8}$ cycloalkyl or heteroaryl bound by $C_{1-3}$ alkyl;

$R^3$ represents respectively unsubstituted or singly or multiply substituted heteroaryl or heteroaryl bound by $C_{1-3}$;

W represents $NR^4$, O or S and
  wherein $R^4$ represents H; saturated or unsaturated, branched or unbranched, unsubstituted or singly or multiply substituted $C_{1-5}$ alkyl; respectively substituted or unsubstituted aryl or heteroaryl; respectively singly or multiply substituted or unsubstituted aryl, heteroaryl or cycloalkyl bound by a $C_{1-3}$ alkyl group; $COR^{12}$; $SO_2R^{12}$;
  wherein $R^{12}$ represents H; respectively saturated or unsaturated, branched or unbranched, singly or multiply substituted or unsubstituted $C_{1-5}$ alkyl; respectively saturated or unsaturated, singly or multiply substituted or unsubstituted $C_{3-8}$ cycloalkyl; respectively singly or multiply substituted or unsubstituted aryl or heteroaryl; or respectively singly or multiply substituted or unsubstituted aryl, $C_{3-8}$ cycloalkyl or heteroaryl bound by $C_{1-3}$ alkyl; $OR^{13}$; $NR^{14}R^{15}$;

$R^5$ represents =O; H; $COOR^{13}$, $CONR^{13}$, $OR^{13}$; saturated or unsaturated, branched or unbranched, unsubstituted or singly or multiply substituted $C_{1-5}$ alkyl; saturated or unsaturated, unsubstituted or singly or multiply substituted $C_{3-8}$ cycloalkyl; unsubstituted or singly or multiply substituted aryl or heteroaryl; or unsubstituted or singly or multiply substituted aryl, $C_{3-8}$ cycloalkyl or heteroaryl bound by $C_{1-3}$ alkyl;

$R^6$ represents H; F, Cl, $NO_2$, $CF_3$, $OR^{13}$, $SR^{13}$, $SO_2R^{13}$, $SO_2OR^{13}$, CN, $COOR^{13}$, $NR^{14}R^{15}$; saturated or unsaturated, branched or unbranched, unsubstituted or singly or multiply substituted $C_{1-5}$ alkyl; saturated or unsaturated, unsubstituted or singly or multiply substituted $C_{3-8}$ cycloalkyl; unsubstituted or singly or multiply substituted aryl or heteroaryl; or unsubstituted or singly or multiply substituted aryl, $C_{3-8}$ cycloalkyl or heteroaryl bound by $C_{1-3}$ alkyl; or $R^5$ and $R^6$ together represent $(CH_2)_n$ where n=2, 3, 4, 5 or 6, wherein individual hydrogen atoms may also be replaced by F, Cl, Br, I, $NO_2$, $CF_3$, $OR^{13}$, CN or $C_{1-5}$ alkyl;

$R^7$, $R^8$, $R^9$ and $R^{10}$ independently represent H, F, Cl, Br, I, $NO_2$, $CF_3$, $OR^{13}$, $SR^{13}$, $SO_2R^{13}$, $SO_2OR^{13}$, CN, $COOR^{13}$, $NR^{14}R^{15}$; unsubstituted or singly or multiply substituted $C_{1-5}$ alkyl, $C_{3-8}$ cycloalkyl; unsubstituted or singly or multiply substituted aryl or heteroaryl; or unsubstituted or singly or multiply substituted aryl, $C_{3-8}$ cycloalkyl or heteroaryl bound by $C_{1-3}$ alkyl;
  wherein $R^{13}$ represents H; respectively saturated or unsaturated, branched or unbranched, unsubstituted or singly or multiply substituted $C_{1-5}$ alkyl; respectively saturated or unsaturated, unsubstituted or singly or multiply substituted $C_{3-8}$ cycloalkyl; unsubstituted or singly or multiply substituted aryl or heteroaryl; or unsubstituted or singly or multiply substituted aryl, $C_{3-8}$ cycloalkyl or heteroaryl bound by $C_{1-3}$ alkyl; and $R^{14}$ and $R^{15}$ independently represent H; respectively saturated or unsaturated, branched or unbranched, unsubstituted or singly or multiply substituted $C_{1-5}$ alkyl; or respectively saturated or unsaturated, unsubstituted or singly or multiply substituted $C_{3-8}$ cycloalkyl; unsubstituted or singly or multiply substituted aryl or heteroaryl; or unsubstituted or singly or multiply substituted aryl, $C_{3-8}$ cycloalkyl or heteroaryl bound by $C_{1-3}$ alkyl; or $R^{14}$ and $R^{15}$ together form $CH_2CH_2OCH_2CH_2$, $CH_2CH_2NR^{16}CH_2CH_2$ or $(CH_2)_{3-6}$,
  wherein $R^{16}$ represents H; saturated or unsaturated, branched or unbranched, unsubstituted or singly or multiply substituted $C_{1-5}$ alkyl;

X represents O, S, SO, SO$_2$ or NR$^{17}$;
   wherein R$^{17}$ represents H; saturated or unsaturated, branched or unbranched C$_{1-5}$ alkyl; COR$^{12}$ or SO$_2$R$^{12}$,
or a physiologically acceptable salt thereof.

2. A compound according to claim 1, wherein said compound is present in the form of a racemic mixture or a mixture of diastereomers or enantiomers.

3. A compound according to claim 1, wherein said compound is present in the form of a pure diastereomer.

4. A compound according to claim 1, wherein R$^1$ and R$^2$ independently represent H, branched or unbranched, saturated or unsaturated, unsubstituted or singly or multiply substituted C$_{1-5}$ alkyl, or CHO.

5. A compound according to claim 1, wherein R$^3$ represents unsubstituted or singly or multiply substituted heteroaryl.

6. A compound according to claim 1, wherein R$^5$ represents H, branched or unbranched, unsubstituted or singly or multiply substituted C$_{1-5}$ alkyl, or COOR$^{13}$, and R$^6$ represents H or C$_{1-5}$ alkyl.

7. A compound according to claim 1, wherein R$^7$, R$^8$, R$^9$ and R$^{10}$ independently represent H; branched or unbranched, unsubstituted or singly or multiply substituted C$_{1-5}$ alkyl; F, Cl, Br, I, CF$_3$, OH, OCH$_3$, NH$_2$, COOH, COOCH$_3$, NHCH$_3$, N(CH$_3$)$_2$ or NO$_2$.

8. A compound according to claim 1, wherein
W represents NR$^4$, O or S;
X represents O, S, SO, SO$_2$ or NR$^{17}$;
R$^1$ and R$^2$ independently represent H; branched or unbranched, singly or multiply substituted or unsubstituted C$_{1-4}$ alkyl; or CHO;
R$^3$ represents unsubstituted or singly or multiply substituted heteroaryl;
R$^4$ represents H, singly or multiply substituted or unsubstituted C$_{1-3}$ alkyl, or CO(CH$_2$)$_m$H, wherein m=0 to 2;
R$^5$ and R$^6$ each represent H; and
R$^7$, R$^8$, R$^9$ and R$^{10}$ independently of one another represent H; respectively branched or unbranched, saturated or unsaturated, unsubstituted or singly or multiply substituted C$_{1-5}$ alkyl or OC$_{1-3}$ alkyl; F, Cl, Br, I, CF$_3$, OH, SH, SCH$_3$, OCH$_3$, NH$_2$, COOH, COOCH$_3$, NHCH$_3$, N(CH$_3$)$_2$ or NO$_2$.

9. A compound according to claim 1, wherein R$^1$ and R$^2$ independently represent H or CH$_3$, and at least one of R$^1$ and R$^2$ is not H.

10. A compound according to claim 1, wherein
W represents NR$^4$;
X represents O;
R$^1$ and R$^2$ independently represent H; branched or unbranched, singly or multiply substituted or unsubstituted C$_{1-4}$ alkyl; or CHO;
R$^3$ represents unsubstituted or singly or multiply substituted heteroaryl;
R$^4$ represents H, singly or multiply substituted or unsubstituted C$_{1-3}$ alkyl, or CO(CH$_2$)$_m$H, wherein m=0 to 2;
R$^5$ and R$^6$ each represent H; and
R$^7$, R$^8$, R$^9$ and R$^{10}$ independently represent H; respectively branched or unbranched, saturated or unsaturated, unsubstituted or singly or multiply substituted C$_{1-5}$ alkyl or OC$_{1-3}$ alkyl; F, Cl, Br, I, CF$_3$, OH, SH, SCH$_3$, OCH$_3$, NH$_2$, COOH, COOCH$_3$, NHCH$_3$, N(CH$_3$)$_2$ or NO$_2$.

11. A compound according to claim 1, wherein R$^3$ represents thienyl or pyridyl.

12. A compound according to claim 1, wherein
R$^5$ represents H, CH$_3$, COOCH$_3$ or CH$_2$OH;
R$^6$ represents H; and
at least two of R$^7$, R$^8$, R$^9$ and R$^{10}$ represent H and the others are independently selected from the group consisting of H; branched or unbranched, unsubstituted or singly or multiply substituted C$_{1-5}$ alkyl; F, Cl, Br, I, OH, OCH$_3$, COOH, COOCH$_3$, NH$_2$, NHCH$_3$, N(CH$_3$)$_2$ and NO$_2$.

13. A compound according to claim 1, wherein R$^1$ and R$^2$ represent CH$_3$, and R$^3$ represents thienyl or pyridyl.

14. A compound according to claim 1, wherein
W represents NR$^4$;
X represents O, and
R$^4$ represents H, CH$_3$, C$_2$H$_5$, acetyl, phenyl, benzyl or COR$^{12}$.

15. A compound according to claim 1, selected from the group consisting of:
1,1-[3-dimethylamino-3-(pyridin-2-yl)pentamethylene]-3,4-dihydro-1H-2,9-diazafluorene,
2-acetyl-1,1-[3-dimethylamino-3-(pyridin-2-yl)pentamethylene]-3,4-dihydro-1H-2,9-diazafluorene,
1,1-[3-dimethylamino-3-(pyridin-2-yl)pentamethylene]-3,4-dihydro-1H-2-oxa-9-thiafluorene,
1,1-[3-dimethylamino-3-(pyridin-2-yl)pentamethylene]-1,3,4,9-tetrahydropyrano-[3,4-b]indole hemicitrate, non-polar diastereoisomer,
1,1-[3-dimethylamino-3-(pyridin-2-yl)pentamethylene]-1,3,4,9-tetrahydropyrano-[3,4-b]indole citrate, polar diastereoisomer,
1,1-[3-dimethylamino-3-(2-thienyl)pentamethylene]-1,3,4,9-tetrahydro-pyrano[3,4-b]indole dimethanesulfonate,
1,1-[3-dimethylamino-3-(2-thienyl)pentamethylene]-1,3,4,9-tetrahydro-pyrano[3,4-b]indole citrate,
1,1-[3-dimethylamino-3-(3-thienyl)pentamethylene]-1,3,4,9-tetrahydro-pyrano[3,4-b]indole hemicitrate,
1,1-[3-dimethylamino-3-(3-thienyl)pentamethylene]-1,3,4,9-tetrahydro-pyrano[3,4-b]indole citrate,
1,1-[3-dimethylamino-3-(2-thienyl)pentamethylene]-1,3,4,9-tetrahydro-pyrano[3,4-b]-6-fluoroindole hemicitrate,
1,1-[3-dimethylamino-3-(2-thienyl)pentamethylene]-1,3,4,9-tetrahydro-pyrano[3,4-b]-6-fluoroindole citrate,
1,1-[3-dimethylamino-3-(3-thienyl)pentamethylene]-1,3,4,9-tetrahydro-pyrano[3,4-b]-6-fluoroindole dimethanesulfonate,
1,1-[3-dimethylamino-3-(3-thienyl)pentamethylene]-1,3,4,9-tetrahydro-pyrano[3,4-b]-6-fluoroindole hemicitrate,
1,1-[3-methylamino-3-(2-thienyl)pentamethylene]-1,3,4,9-tetrahydro-pyrano[3,4-b]indole citrate,
1,1-[3-methylamino-3-(2-thienyl)pentamethylene]-1,3,4,9-tetrahydro-pyrano[3,4-b]-6-fluoroindole citrate,
1,1-[3-methylamino-3-(3-thienyl)pentamethylene]-1,3,4,9-tetrahydro-pyrano[3,4-b]indole citrate, and
1,1-[3-methylamino-3-(3-thienyl)pentamethylene]-1,3,4,9-tetrahydro-pyrano[3,4-b]-6-fluoroindole citrate;
or a mixture of two or more of the foregoing.

16. A process for producing a compound according to claim 1, said process comprising reacting an educt corresponding to formula A

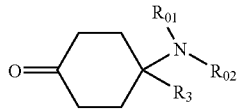

wherein $R^{01}$ and $R^{02}$ have the meaning given in claim 1 for $R^2$ or represent a protective group, and $R^3$ has the meaning given in claim 1 for $R^3$,
with addition of an acid or a trimethylsilylester of an acid, in a solvent,
with an educt corresponding to formula B

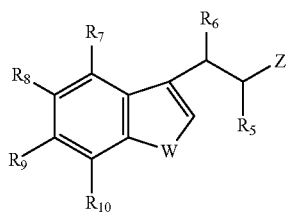

Z = XY
Y = H, SiMe$_3$ wherein W, X and $R^5$ to $R^{10}$ have the meanings given in claim 1.

17. A process according to claim 16, wherein said acid or trimethylsilylester of an acid is selected from the group consisting of trifluoromethane sulfonic acid trimethylsilylester, trifluoromethane sulfonic acid, acetic acid, phosphoric acid, methane sulfonic acid, and trifluoroacetic acid, and said solvent is selected from the group consisting of dichloroethane, dichloromethane, chloroform, acetonitrile, diethyl ether and nitromethane.

18. A process for producing a spirocyclic cyclohexane compound according to claim 1, wherein X represents $NR^{17}$, and $R^{17}$ represents $COR^{12}$ or $SO_2R^2$, said process comprising reacting a compound corresponding to formula I in which X represents NH,
with the addition of a base,
with an anhydride or an acid chloride.

19. A process according to claim 18, wherein said base is triethylamine, and said reaction is carried out under microwave irradiation.

20. A process for producing a spirocyclic cyclohexane compound according to claim 1, wherein X represents SO or SO$_2$, said process comprising oxidizing a compound corresponding to formula I in which X represents S, with an oxidizing agent.

21. A process according to claim 20, wherein said oxidizing agent is H$_2$O$_2$.

22. A process for producing a spirocyclic cyclohexane compound corresponding to formula Ib

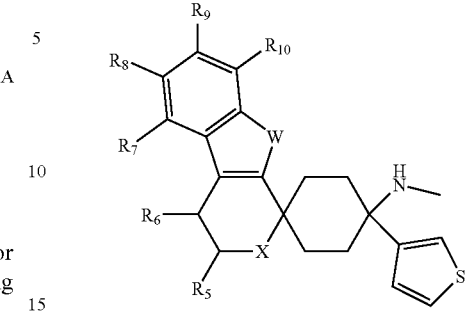

said process comprising
reacting thiophen-3-yl-acetonitrile with an acrylic ester or a 3-bromopropionic acid ester,
hydrolyzing and decarboxylating the ester,
providing the hydrolyzed and decarboxylated product with protective groups,
converting the nitrile group into a carboxylic acid group and then into an isocyanate by hydrolysis followed by reaction with a reducing agent,
removing protective groups by addition of acid or a trimethylsilylester of an acid, and
reacting the resulting product in a solvent with an educt of general formula B

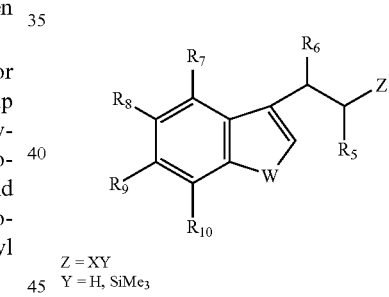

Z = XY
Y = H, SiMe$_3$ wherein W, X and $R^5$ to $R^{10}$ have the meanings given in claim 1.

23. A process according to claim 22, wherein the reducing agent is lithium aluminium hydride, the acid or trimethylsilylester is selected from the group consisting of trifluoromethane sulfonic acid trimethylsilylester, trifluoromethane sulfonic acid, acetic acid, phosphoric acid, methane sulfonic acid and trifluoroacetic acid, and the solvent is selected from the group consisting of dichloroethane, dichloromethane, chloroform, acetonitrile, diethyl ether and nitromethane.

24. A pharmaceutical composition comprising a spirocyclic cyclohexane compound according to claim 1, and at least one pharmaceutical auxiliary agent.

25. A method of treating pain in a patient in need thereof, said method comprising administering to said patient a pharmaceutically effective amount of a compound according to claim 1.

26. A method according to claim 25, wherein said pain is acute pain, neuropathic pain or chronic pain.

27. A method of treating withdrawal symptoms of opioid abuse, dependency or addiction, in a patient in need thereof, said method comprising administering to said patient a pharmaceutically effective amount of a compound according to claim 1.

28. A method according to claim 27, wherein said condition is opioid addiction.

29. A method according to claim 27, wherein said compound, is co-administered with an opioid to reduce the addiction potential of the opioid.

* * * * *